United States Patent
Pirim et al.

(10) Patent No.: US 6,717,518 B1
(45) Date of Patent: Apr. 6, 2004

(54) METHOD AND APPARATUS FOR DETECTION OF DROWSINESS

(75) Inventors: Patrick Pirim, Paris (FR); Thomas Binford, Cupertino, CA (US)

(73) Assignee: Holding B.E.V.S.A., Luxembourg (LU)

( * ) Notice: Subject to any disclaimer, the term of this patent is extended or adjusted under 35 U.S.C. 154(b) by 0 days.

(21) Appl. No.: 09/600,390

(22) PCT Filed: Jan. 15, 1999

(86) PCT No.: PCT/EP99/00300

§ 371 (c)(1),
(2), (4) Date: Feb. 9, 2001

(87) PCT Pub. No.: WO99/36893

PCT Pub. Date: Jul. 22, 1999

(30) Foreign Application Priority Data

Jan. 15, 1998 (FR) .............................................. 98 00378
Aug. 25, 1998 (WO) ................................ PCT/EP98/05383

(51) Int. Cl.⁷ ................................................ G08B 23/00
(52) U.S. Cl. ...................... 340/576; 348/143; 382/117
(58) Field of Search ................................. 340/575, 576; 382/100, 103, 115, 117; 348/143, 148, 672

(56) References Cited

U.S. PATENT DOCUMENTS

| | | | |
|---|---|---|---|
| 4,259,665 A | 3/1981 | Manning | 340/575 |
| 4,485,375 A | 11/1984 | Hershberger | 340/576 |
| 4,555,697 A | 11/1985 | Thackrey | 340/575 |
| 4,928,090 A | 5/1990 | Yoshimi et al. | 340/575 |
| 5,195,606 A | 3/1993 | Martyniuk | 180/272 |
| 5,218,387 A * | 6/1993 | Ueno et al. | 351/210 |
| 5,353,013 A | 10/1994 | Estrada | 340/575 |
| 5,402,109 A | 3/1995 | Mannik | 340/575 |
| 5,469,143 A | 11/1995 | Cooper | 340/575 |
| 5,481,622 A * | 1/1996 | Gerhardt et al. | 382/103 |
| 5,682,144 A | 10/1997 | Mannik | 340/575 |
| 5,684,461 A | 11/1997 | Jones | 340/575 |
| 5,689,241 A | 11/1997 | Clarke, Sr. et al. | 340/575 |
| 5,786,765 A * | 7/1998 | Kumakura et al. | 340/576 |
| 5,813,993 A | 9/1998 | Kaplan et al. | 600/544 |
| 5,841,354 A | 11/1998 | Bae et al. | 340/575 |
| 5,859,921 A * | 1/1999 | Suzuki | 382/118 |
| 5,878,156 A * | 3/1999 | Okumura | 382/118 |
| 6,304,187 B1 * | 10/2001 | Pirim | 340/576 |

FOREIGN PATENT DOCUMENTS

| | | | |
|---|---|---|---|
| DE | 19715519 A1 | 11/1997 | G08B/21/00 |
| WO | WO 97/01246 | 1/1997 | H04N/7/18 |
| WO | WO 98/05002 | 2/1998 | G06T/7/20 |

OTHER PUBLICATIONS

Ueno, H. et al.: "Development of Drowsiness Detection System" 1994 Vehicle Navigation & Information Systems Conference Proceedings, pp. 15–20, XP 000641294, Aug. 1994.

* cited by examiner

*Primary Examiner*—Thomas Mullen
(74) *Attorney, Agent, or Firm*—Townsend and Townsend and Crew LLP

(57) ABSTRACT

In a process of detecting a person falling asleep, an image of the face of the person is acquired. Pixels of the image having characteristics corresponding to an eye of the person are selected and a histogram is formed of the selected pixels. The histogram is analyzed over time to identify each opening and closing of the eye, and characteristics indicative of the person falling asleep are determined. A sub-area of the image including the eye may be determined by identifying the head or a facial characteristic of the person, and then identifying the sub-area using an anthropomorphic model. To determine openings and closings of the eyes, histograms of shadowed pixels of the eye are analyzed to determine the width and height of the shadowing, or histograms of movement corresponding to blinking are analyzed. An apparatus for detecting a person falling asleep includes a sensor for acquiring an image of the face of the person, a controller, and a histogram formation unit for forming a histogram on pixels having selected characteristics. Also disclosed is a rear-view mirror assembly incorporating the apparatus.

39 Claims, 20 Drawing Sheets

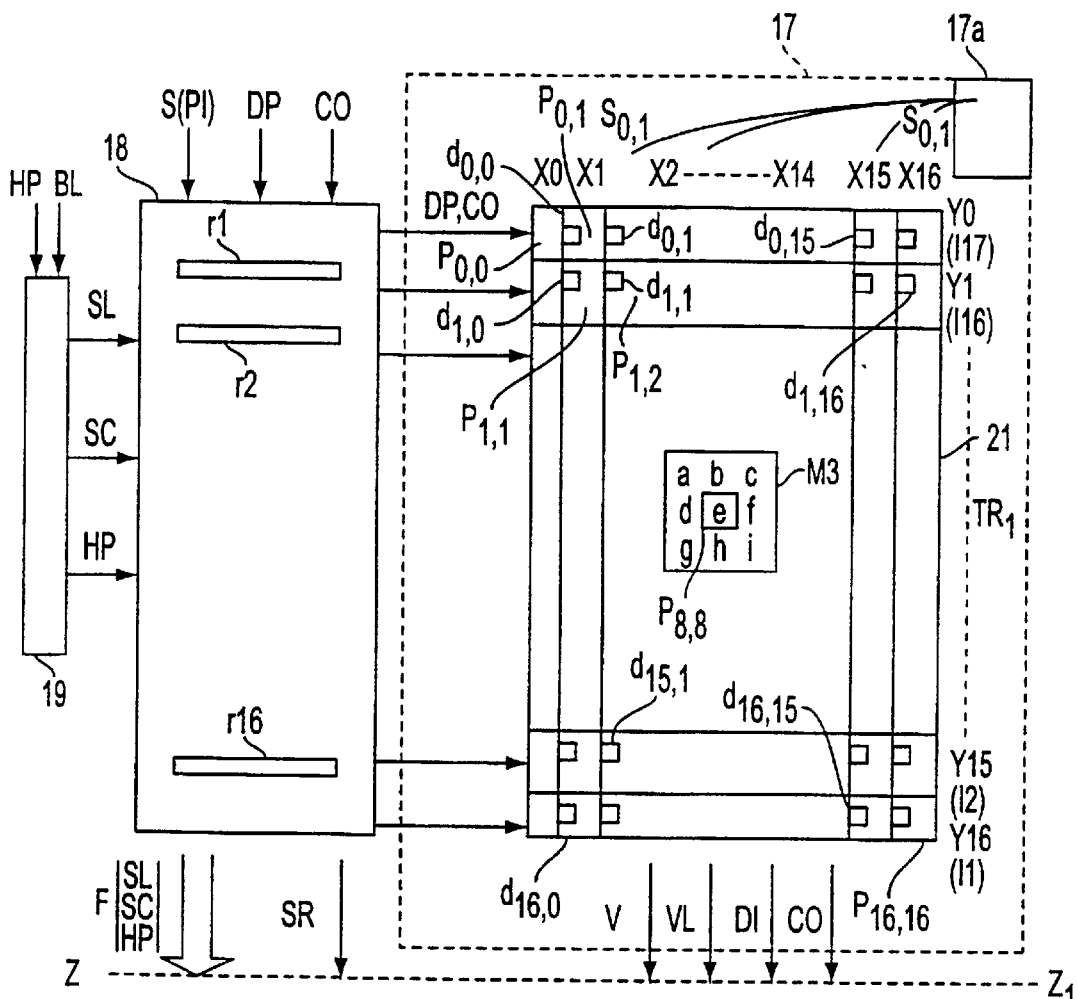
FIG. 4
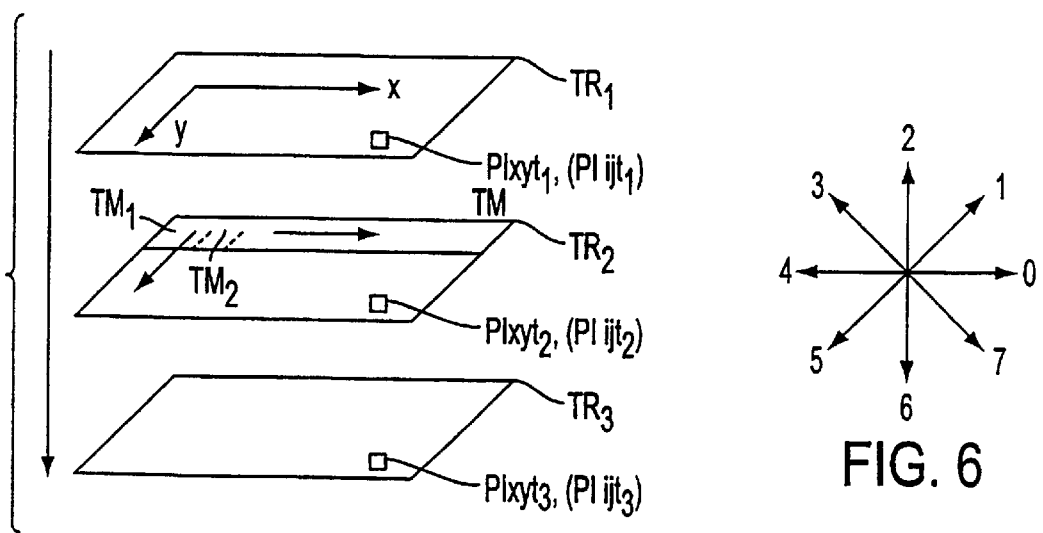
FIG. 5
FIG. 6

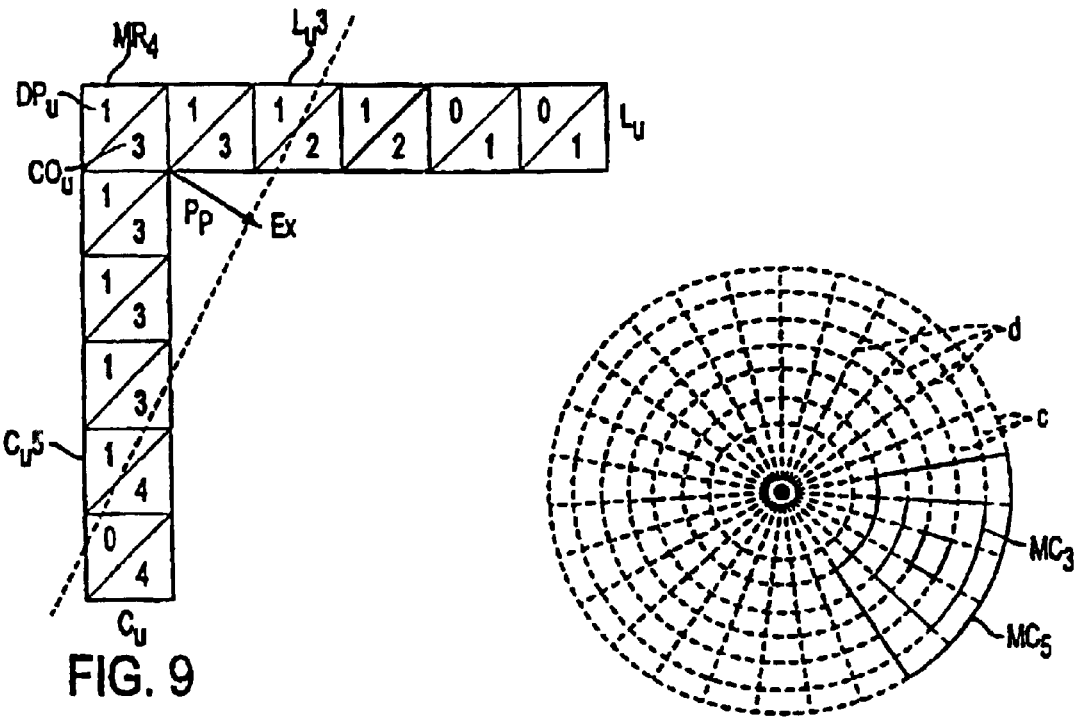
FIG. 9
FIG. 10
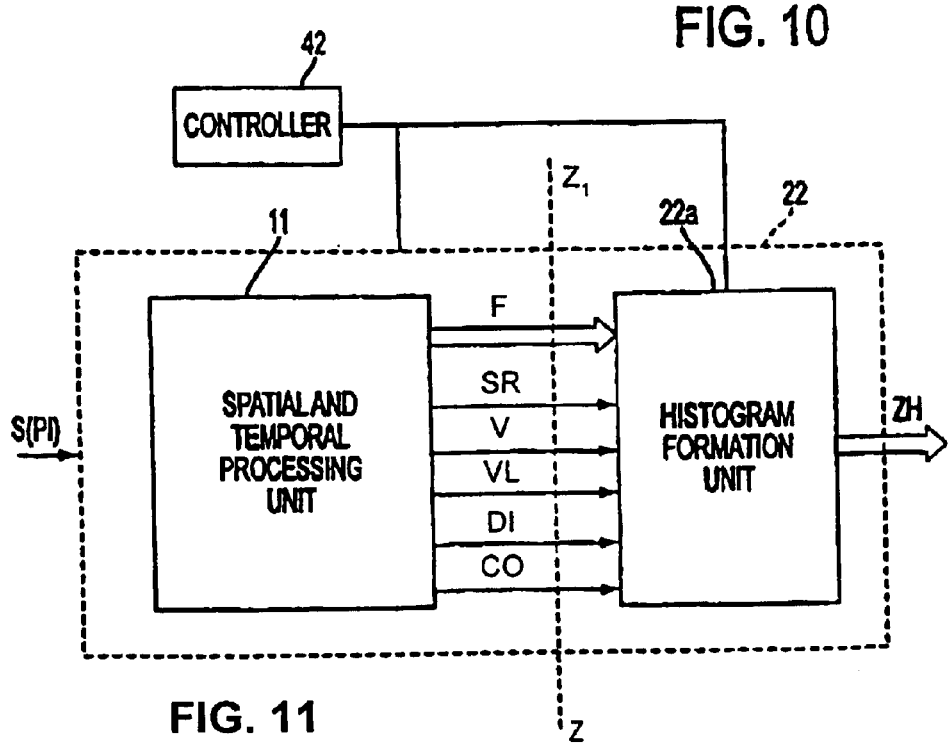
FIG. 11

METHOD AND APPARATUS FOR DETECTION OF DROWSINESS

BACKGROUND OF THE INVENTION

1. Field of the Invention

The present invention relates generally to an image processing system, and more particularly to the use of a generic image processing system to detect drowsiness.

2. Description of the Related Art

It is well known that a significant number of highway accidents result from drivers becoming drowsy or falling asleep, which results in many deaths and injuries. Drowsiness is also a problem in other fields, such as for airline pilots and power plant operators, in which great damage may result from failure to stay alert A number of different physical criteria may be used to establish when a person is drowsy, including a change in the duration and interval of eye blinking. Normally, the duration of bilking is about 100 to 200 ms when awake and about 500 to 800 ms when drowsy. The time interval between successive blinks is generally constant while awake, but varies within a relatively broad range when drowsy.

Numerous devices have been proposed to detect drowsiness of drivers. Such devices are shown, for example, in U.S. Pat. Nos. 5,841,354; 5,813,993; 5,689,241; 5,684,461; 5,682,144; 5,469,143; 5,402,109; 5,353,013; 5,195,606; 4,928,090; 4,555,697, 4,485,375; and 4,259,665. In general, these devices fall into three categories: i) devices that detect movement of the head of the driver, e.g., tilting; ii) devices that detect a physiological change in the driver, e.g., altered heartbeat or brething, and iii) divice that detect a physical result of the driver falling asleep, e.g., a reduced grip of the steering wheel. None of this device is believed to have met with commercial success.

The German patent application DE 19715519 and the corresponding French patent application FR-2.747.346 disclose an apparatus and process of evaluation of the drowsiness level of a driver using a video camera placed near the feet of the driver and a processing unit for processing the camera image with software detecting the blinks of the eyes to determine the time gap between the beginning and the end of the blinks. More particularly, a unit of the processor realizes a memorization of the video image and its treatment, so as so determine an area comprising the driver's eyes, the dectetion of the time gap between the closing oft he driver ayelids and their full opening and a treatment in a memo and a processor in combination with the unit to calculate a ratio of slow blink apparition.

The object of the international patent application published WO-97/01246 is a security system comprising a video camera placed within the rear-view mirror of a car and a video screen remotely disposed for the analysis of what is happening in the car and around it, as well as of what happened due to the recording of the output video signal of the camera This is in fact a concealed camera (within the rear-view mirror), so that it is imperceptible to vandals and thieves and which observes a large scope including the inside of the car and its surroundings, the record allowing one to know later what has happened in this scope (page 6, lines 13 to 19), this is not a detector whose effective angle is strictly limited to the car driver face in order to detect its eventual drowsiness and to make him awake.

Commonly-owned PCT Application Ser. Nos. PCT/FR97/ 01354 and PCT/EP98/05383 disclose a generic image processing system that operates to localize objects in relative movement in an image and to determine the speed and direction of the objects in real-time. Each pixel of an image is smoothed using its own time constant. A binary value corresponding to the existence of a significant variation in the amplitude of the smoothed pixel from the prior frame, and the amplitude of the variation, are determined, and the time constant for the pixel is updated. For each particular pixel, two matrices are formed that include a subset of the pixels spatially related to the particular pixel. The first matrix contains the binary values of the subset of pixels. The second matrix contains the amplitude of the variation of the subset of pixels. In the first matrix, it is determined whether the pixels along an oriented direction relative to the particular pixel have binary values representative of significant variation, and, for such pixels, it is determined in the second matrix whether the amplitude of these pixels varies in a known manner indicating movement in the oriented direction. In domains that include luminance, hue, saturation, speed, oriented direction, time constant, and x and y position, a histogram is formed of the values in the first and second matrices falling in user selected combinations of such domains. Using the histograms, it is determined whether there is an area having the characteristics of the selected combinations of domains.

It would be desirable to apply such a generic image processing system to detect the drowsiness of a person.

SUMMARY OF THE INVENTION

The present invention is a process of detecting a driver falling asleep in which an image of the face of the driver is acquired. Pixels of the image having characteristics corresponding to characteristics of at least one eye of the driver are selected and a histogram is formed of the selected pixels. The histogram is analyzed over time to identify each opening and closing of the eye, and from the eye opening and closing information, characteristics indicative of a driver falling asleep are determined.

In one embodiment, a sub-area of the image comprising the eye is determined prior to the step of selecting pixels of the image having characteristics corresponding to characteristics of an eye. In this embodiment, the step of selecting pixels of the image having characteristics of an eye involves selecting pixels within the sub-area of the image. The step of identifying a sub-area of the image preferably involves identifying the head of the driver, or a facial characteristic of the driver, such as the driver's nostrils, and then identifying the sub-area of the image using an anthropomorphic model. The head of the driver may be identified by selecting pixels of the image having characteristics corresponding to edges of the head of the driver. Histograms of the selected pixels of the edges of the driver's head are projected onto orthogonal axes. These histograms are then analyzed to identify the edges of the driver's head.

The facial characteristic of the driver may be identified by selecting pixels of the image having characteristics corresponding to the facial characteristic. Histograms of the selected pixels of the facial characteristic are projected onto orthogonal axes. These histograms are then analyzed to identify the facial characteristic. If desired, the step of identifying the facial characteristic in the image involves searching sub-images of the image until the facial characteristic is found. In the case in which the facial characteristic is the nostrils of the driver, a histogram is formed of pixels having low luminance levels to detect the nostrils. To confirm detection of the nostrils, the histograms of the nostril pixels may be analyzed to determine whether the spacing between the nostrils is within a desired range and whether the dimensions of the nostrils fall within a desired range. In order to confirm the identification of the facial characteristic, an anthropomorphic model and the location of the facial characteristic are used to select a sub-area of the image containing a second facial characteristic. Pixels of the image having characteristics corresponding to the second facial characteristic are selected and histograms of the selected pixels of the second facial characteristic are analyzed to confirm the identification of the first facial characteristic.

In order to determine openings and closings of the eyes of the driver, the step of selecting pixels of the image having characteristics corresponding to characteristics of an eye of the driver involves selecting pixels having low luminance levels corresponding to shadowing of the eye. In this embodiment, the step of analyzing the histogram over time to identify each opening and closing of the eye involves analyzing the shape of the eye shadowing to determine openings and closings of the eye. The histograms of shadowed pixels are preferably projected onto orthogonal axes, and the step of analyzing the shape of the eye shadowing involves analyzing the width and height of the shadowing.

An alternative method of determining openings and closings of the eyes of the driver involves selecting pixels of the image having characteristics of movement corresponding to blinking. In this embodiment, the step of analyzing the histogram over time to identify each opening and closing of the eye involves analyzing the number of pixels in movement corresponding to blinking over time. The characteristics of a blinking eye are preferably selected from the group consisting of i) DP=1, ii) CO indicative of a blinking eyelid, iii) velocity indicative of a blinking eyelid, and iv) up and down movement indicative of a blinking eyelid.

An apparatus for detecting a driver falling asleep includes a sensor for acquiring an image of the face of the driver, a controller, and a histogram formation unit for forming a histogram on pixels having selected characteristics. The controller controls the histogram formation unit to select pixels of the image having characteristics corresponding to characteristics of at least one eye of the driver and to form a histogram of the selected pixels. The controller analyzes the histogram over time to identifies each opening and closing of the eye, and determines from the opening and closing information on the eye, characteristics indicative of the driver falling asleep.

In one embodiment, the controller interacts with the histogram formation unit to identify a sub-area of the image comprising the eye, and the controller controls the histogram formation unit to select pixels of the image having characteristics corresponding to characteristics of the eye only within the sub-area of the image. In order to select the sub-area of the image, the controller interacts with the histogram formation unit to identify the head of the driver in the image, or a facial characteristic of the driver, such as the driver's nostrils. The controller then identifies the sub-area of the image using an anthropomorphic model. To identify the head of the driver, the histogram formation unit selects pixels of the image having characteristics corresponding to edges of the head of the driver and forms histograms of the selected pixels projected onto orthogonal axes. To identify a facial characteristic of the driver, the histogram formation unit selects pixels of the image having characteristics corresponding to the facial characteristic and forms histograms of the selected pixels projected onto orthogonal axes. The controller then analyzes the histograms of the selected pixels to identify the edges of the head of the driver or the facial characteristic, as the case may be. If the facial characteristic is the nostrils of the driver, the histogram formation unit selects pixels of the image having low luminance levels corresponding to the luminance level of the nostrils. The controller may also analyze the histograms of the nostril pixels to determine whether the spacing between the nostrils is within a desired range and whether dimensions of the nostrils fall within a desired range. If desired, the controller may interact with the histogram formation unit to search sub-images of the image to identify the facial characteristic.

In order to verify identification of the facial characteristic, the controller uses an anthropomorphic model and the location of the facial characteristic to cause the histogram formation unit to select a sub-area of the image containing a second facial characteristic. The histogram formation unit selects pixels of the image in the sub-area having characteristics corresponding to the second facial characteristic and forms a histogram of such pixels. The controller then analyzes the histogram of the selected pixels corresponding to the second facial characteristic to identify the second facial characteristic and to thereby confirm the identification of the first facial characteristic.

In one embodiment, the histogram formation unit selects pixels of the image having low luminance levels corresponding to shadowing of the eyes, and the controller then analyzes the shape of the eye shadowing to identify shapes corresponding to openings and closings of the eye. The histogram formation unit preferably forms histograms of the shadowed pixels of the eye projected onto orthogonal axes, and the controller analyzes the width and height of the shadowing to determine openings and closings of the eye.

In an alternative embodiment, the histogram formation unit selects pixels of the image in movement corresponding to blinking and the controller analyzes the number of pixels in movement over time to determine openings and closings of the eye. The characteristics of movement corresponding to blinking are preferably selected from the group consisting of i) DP=1, ii) CO indicative of a blinking eyelid, iii) velocity indicative of a blinking eyelid, and iv) up and down movement indicative of a blinking eyelid.

If desired, the sensor may be integrally constructed with the controller and the histogram formation unit. The apparatus may comprise an alarm, which the controller operates upon detection of the driver falling asleep, and may comprise an illumination source, such as a source of IR radiation, with the sensor being adapted to view the driver when illuminated by the illumination source.

A rear-view mirror assembly comprises a rear-view mirror and the described apparatus for detecting driver drowsiness mounted to the rear-view mirror. In one embodiment, a bracket attaches the apparatus to the rear-view mirror. In an alternative embodiment, the rear-view mirror comprises a housing having an open side and an interior. The rear-view mirror is mounted to the open side of the housing, and is see-through from the interior of the housing to the exterior of the housing. The drowsiness detection apparatus is mounted interior to the housing with the sensor directed toward the rear-view mirror. If desired, a joint attaches the apparatus to the rear-view mirror assembly, with the joint being adapted to maintain the apparatus in a position facing the driver during adjustment of the mirror assembly by the driver. The rear-view mirror assembly may include a source of illumination directed toward the driver, with the sensor adapted to view the driver when illuminated by the source of illumination. The rear-view mirror assembly may also include an alarm, with the controller operating the alarm upon detection of the driver falling asleep. Also disclosed is a vehicle comprising the drowsiness detection device.

BRIEF DESCRIPTION OF THE DRAWINGS

FIG. 4 is a block diagram of the spatial processing unit of the invention.

FIG. 5 is a diagram showing the processing of pixels in accordance with the invention.

FIG. 6 illustrates the numerical values of the Freeman code used to determine movement direction in accordance with the invention.

FIG. 9 illustrates reverse-L matrices as processed by the temporal processing unit.

FIG. 10 illustrates angular sector shaped matrices as processed by the temporal processing unit.

FIG. 11 is a block diagram showing the relationship between the temporal and spatial processing units, and the histogram formation units.

DETAILED DESCRIPTION OF THE INVENTION

The present invention discloses an application of the generic image processing system disclosed in commonly-owned PCT Application Serial Nos. PCT/FR97/01354 and PCT/EP98/05383, the contents of which are incorporated herein by reference for detection of various criteria associated with the human eye, and especially to detection that a driver is falling asleep while driving a vehicle.

Figure 1:
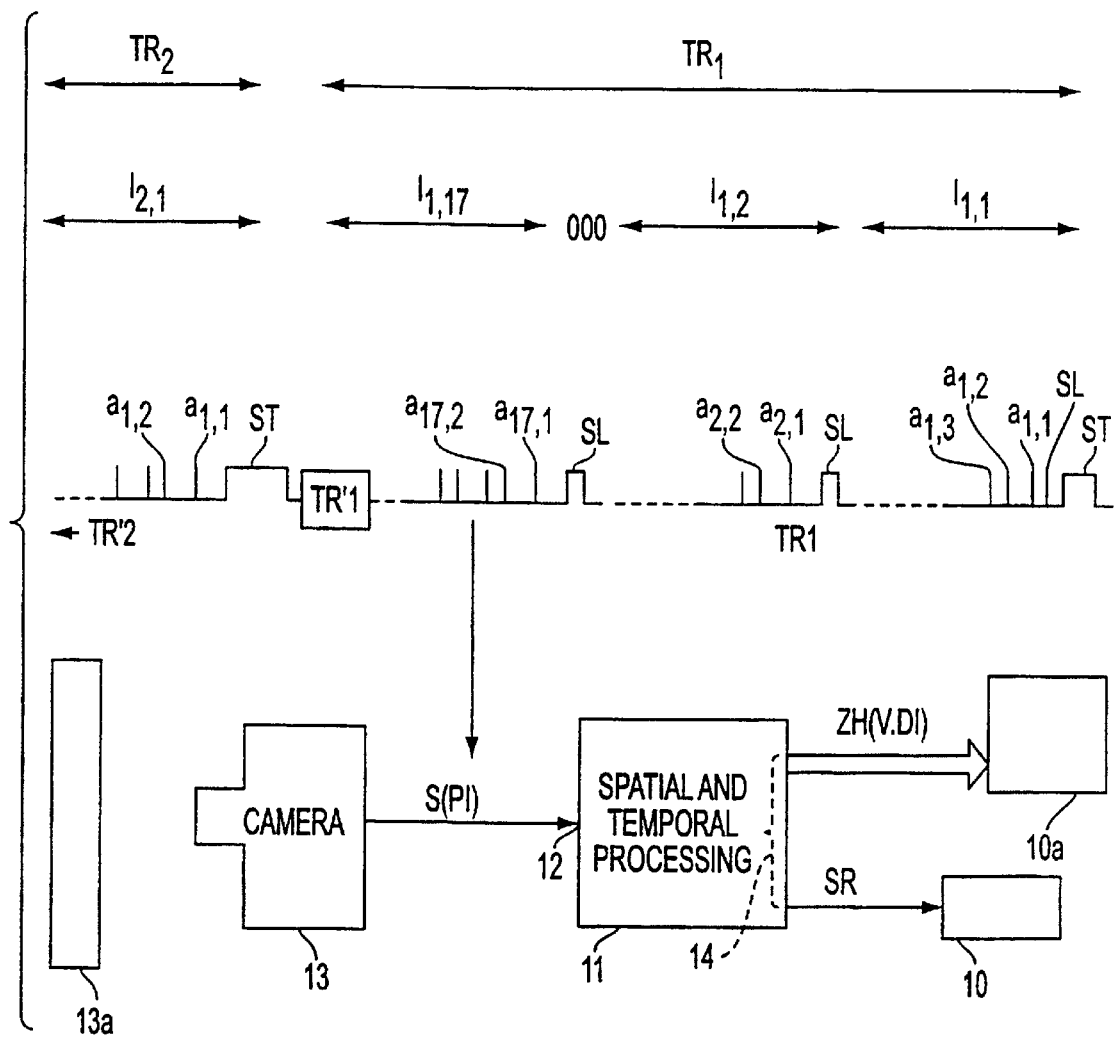
FIG. 1 is a diagrammatic illustration of the system according to the invention.

The apparatus of the invention is similar to that described in the aforementioned PCT application Ser. Nos. PCT/FR97/01354 and PCT/EP98/05383, which will be described herein for purposes of clarity. Referring to FIGS. 1 and 11, the generic image processing system 22 includes a spatial and temporal processing unit 11 in combination with a histogram formation unit 22a. Spatial and temporal processing unit 11 includes an input 12 that receives a digital video signal S originating from a video camera or other imaging device 13 which monitors a scene 13a. Imaging device 13 is preferably a conventional CMOS-type CCD camera, which for purposes of the presently-described invention is mounted on a vehicle facing the driver. It will be appreciated that when used in non-vehicular applications, the camera may be mounted in any desired fashion to detect the specific criteria of interest. It is also foreseen that any other appropriate sensor, e.g., ultrasound, IR, Radar, etc., may be used as the imaging device. Imaging device 13 may have a direct digital output, or an analog output that is converted by an A/D converter into digital signal S. Imaging device 13 may also be integral with generic image processing system 22, if desired, for example as represented by element 13A.

While signal S may be a progressive signal, it is preferably composed of a succession of pairs of interlaced frames, $TR_1$ and $TR'_1$ and $TR_2$ and $TR'_2$, each consisting of a succession of horizontal scanned lines, e.g., $l_{1.1}, l_{1.2}, \ldots, l_{1.17}$ in $TR_1$, and $l_{2.1}, TR_2$. Each line consists of a succession of pixels or image points PI, e.g., $a_{1.1}, a_{1.2}$ and $a_{1.3}$ for line $l_{1.1}$; $a_{17.1}$ and $al_{17.2}$ for line $l_{1.7}$; $a_{1.1}$ and $a_{1.2}$ for line $l_{2.1}$. Signal S(PI) represents S composed of pixels PI.

S(PI) includes a frame synchronization signal (ST) at the beginning of each frame, a line synchronization signal (SL)

at the beginning of each line, and a blanking signal (BL). Thus, S(PI) includes a succession of frames, which are representative of the time domain, and within each frame, a series of lines and pixels, which are representative of the spatial domain.

In the time domain, "successive frames" shall refer to successive frames of the same type (i.e., odd frames such as $TR_1$ or even frames such as $TR'_1$), and "successive pixels in the same position" shall denote successive values of the pixels (PI) in the same location in successive frames of the same type, e.g., $a_{1.1}$ of $l_{1.1}$ in frame $TR_1$ and $a_{1.1}$ of $l_{1.1}$ in the next corresponding frame $TR_2$.

Spatial and temporal processing unit 11 generates outputs ZH and SR 14 to a data bus 23 (FIG. 12), which are preferably digital signals. Complex signal ZH comprises a number of output signals generated by the system, preferably including signals indicating the existence and localization of an area or object in motion, and the speed V and the oriented direction of displacement DI of each pixel of the image. Also preferably output from the system is input digital video signal S, which is delayed (SR) to make it synchronous with the output ZH for the frame, taking into account the calculation time for the data in composite signal ZH (one frame). The delayed signal SR is used to display the image received by camera 13 on a monitor or television screen 10, which may also be used to display the information contained in composite signal ZH. Composite signal ZH may also be transmitted to a separate processing assembly 10a in which further processing of the signal may be accomplished.

Figure 2:
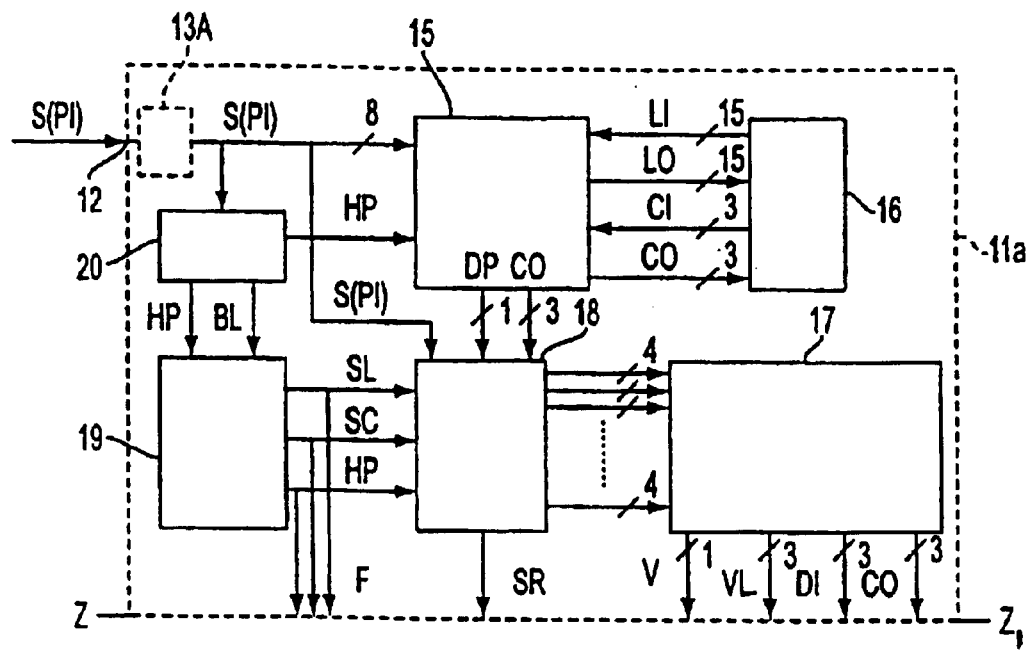
FIG. 2 is a block diagram of the temporal and spatial processing units of the invention.

Referring to FIG. 2, spatial and temporal processing unit 11 includes a first assembly 11a, which consists of a temporal processing unit 15 having an associated memory 16, a spatial processing unit 17 having a delay unit 18 and sequencing unit 19, and a pixel clock 20, which generates a clock signal HP, and which serves as a clock for temporal processing unit 15 and sequencing unit 19. Clock pulses HP are generated by clock 20 at the pixel rate of the image, which is preferably 13.5 MHZ.

Figure 3:
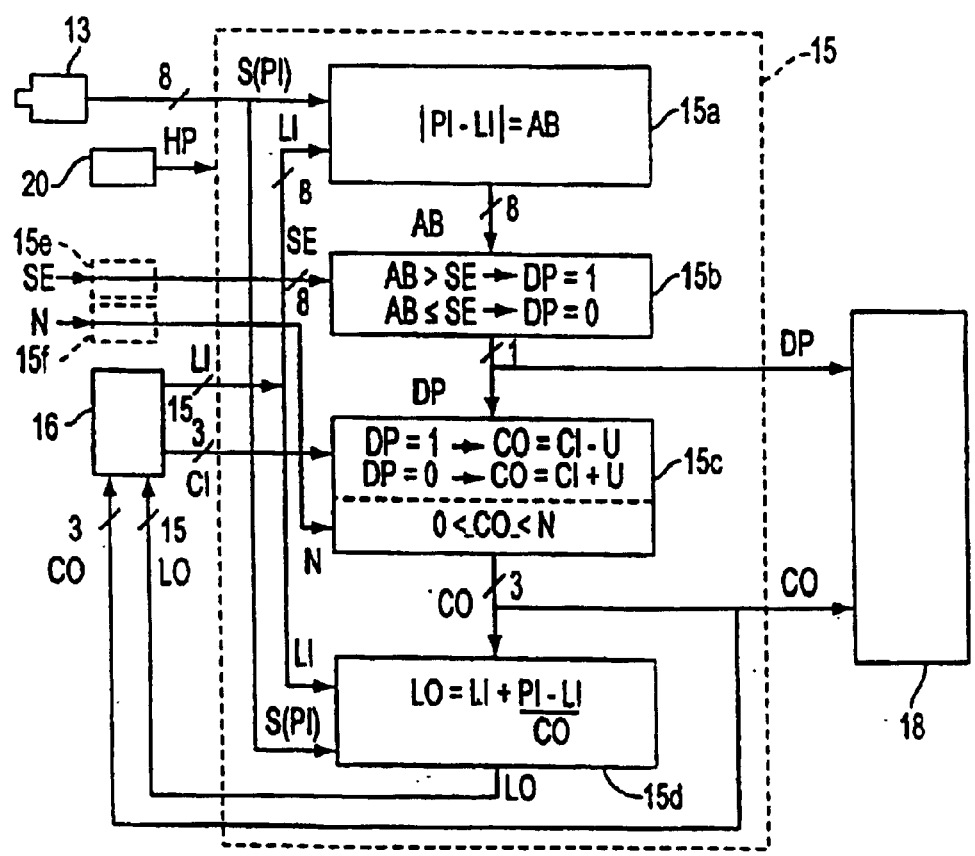
FIG. 3 is a block diagram of the temporal processing unit of the invention.

FIG. 3 shows the operation of temporal processing unit 15, the function of which is to smooth the video signal and generate a number of outputs that are utilized by spatial processing unit 17. During processing, temporal processing unit 15 retrieves from memory 16 the smoothed pixel values LI of the digital video signal from the immediately prior frame, and the values of a smoothing time constant CI for each pixel. As used herein, LO and CO shall be used to denote the pixel values (L) and time constants (C) stored in memory 16 from temporal processing unit 15, and LI and CI shall denote the pixel values (L) and time constants (C) respectively for such values retrieved from memory 16 for use by temporal processing unit 15. Temporal processing unit 15 generates a binary output signal DP for each pixel, which identifies whether the pixel has undergone significant variation, and a digital signal CO, which represents the updated calculated value of time constant C.

Referring to FIG. 3, temporal processing unit 15 includes a first block 15a which receives the pixels PI of input video signal S. For each pixel PI, the temporal processing unit 15 retrieves from memory 16 a smoothed value LI of this pixel from the immediately preceding corresponding frame, which was calculated by temporal processing unit 15 during processing of the immediately prior frame and stored in memory 16 as LO. Temporal processing unit 15 calculates the absolute value AB of the difference between each pixel value PI and LI for the same pixel position (for example $a_{1.1}$, of $l_{1.1}$ in $TR_1$ and of $l_{1.1}$ in $TR_2$:

$$AB=|PI-LI|$$

Temporal processing unit 15 is controlled by clock signal HP from clock 20 in order to maintain synchronization with the incoming pixel stream. Test block 15b of temporal processing unit 15 receives signal AB and a threshold value SE. Threshold SE may be constant, but preferably varies based upon the pixel value PI, and more preferably varies with the pixel value so as to form a gamma correction. Known means of varying SE to form a gamma correction is represented by the optional block 15e shown in dashed lines. Test block 15b compares, on a pixel-by-pixel basis, digital signals AB and SE in order to determine a binary signal DP. If AB exceeds threshold SE, which indicates that pixel value PI has undergone significant variation as compared to the smoothed value LI of the same pixel in the prior frame, DP is set to "1" for the pixel under consideration. Otherwise, DP is set to "0" for such pixel.

When DP=1, the difference between the pixel value PI and smoothed value LI of the same pixel in the prior frame is considered too great, and temporal processing unit 15 attempts to reduce this difference in subsequent frames by reducing the smoothing time constant C for that pixel. Conversely, if DP=0, temporal processing unit 15 attempts to increase this difference in subsequent frames by increasing the smoothing time constant C for that pixel. These adjustments to time constant C as a function of the value of DP are made by block 15c If DP=1, block 15c reduces the time constant by a unit value U so that the new value of the time constant CO equals the old value of the constant CI minus unit value U.

$$CO=CI-U$$

If DP=0, block 15c increases the time constant by a unit value U so that the new value of the time constant CO equals the old value of the constant CI plus unit value U.

$$CO=CI+U$$

Thus, for each pixel, block 15c receives the binary signal DP from test unit 15b and time constant CI from memory 16, adjusts CI up or down by unit value U, and generates a new time constant CO which is stored in memory 16 to replace time constant CI.

In a preferred embodiment, time constant C, is in the form $2^P$, where p is incremented or decremented by unit value U, which preferably equals 1, in block 15c. Thus, if DP=1, block 15c subtracts one (for the case where U=1) from p in the time constant $2^P$ which becomes $2^{P-1}$. If DP=0, block 15c adds one to p in time constant $2^P$, which becomes $2^{P+1}$. The choice of a time constant of the form $2^P$ facilitates calculations and thus simplifies the structure of block 15c.

Block 15c includes several tests to ensure proper operation of the system. First, CO must remain within defined limits. In a preferred embodiment, CO must not become negative (CO$\geq$0) and it must not exceed a limit N (CO$\leq$N), which is preferably seven.

In the instance in which CI and CO are in the form $2^P$, the upper limit N is the maximum value for p.

The upper limit N may be constant, but is preferably variable. An optional input unit 15f includes a register of memory that enables the user, or controller 42 to vary N.

The consequence of increasing N is to increase the sensitivity of the system to detecting displacement of pixels, whereas reducing N improves detection of high speeds. N may be made to depend on PI (N may vary on a pixel-by-pixel basis, if desired) in order to regulate the variation of LO as a function of the lever of PI, i.e., $N_{ijt}=f(PI_{ijt})$, the calculation of which is done in block 15f, which in this case would receive the value of PI from video camera 13.

Finally, a calculation block 15d receives, for each pixel, the new time constant CO generated in block 15c, the pixel values PI of the incoming video signal S, and the smoothed pixel value LI of the pixel in the previous frame from memory 16. Calculation block 15d then calculates a new smoothed pixel value LO for the pixel as follows:

$$LO=LI+(PI-LI)/CO$$

If $CO=2^p$, then $$LO=LI+(PI-LI)/2^{po}$$

where "po", is the new value of p calculated in unit 15c and which replaces previous value of "pi" in memory 16.

The purpose of the smoothing operation is to normalize variations in the value of each pixel PI of the incoming video signal for reducing the variation differences. For each pixel of the frame, temporal processing unit 15 retrieves LI and CI from memory 16, and generates new values LO (new smoothed pixel value) and CO (new time constant) that are stored in memory 16 to replace LI and CI respectively. As shown in FIG. 2, temporal processing unit 15 transmits the CO and DP values for each pixel to spatial processing unit 17 through the delay unit 18.

The capacity of memory 16 assuming that there are R pixels in a frame, and therefore 2R pixels per complete image, must be at least 2R(e+f) bits, where e is the number of bits required to store a single pixel value LI (preferably eight bits), and f is the number of bits required to store a single time constant CI (preferably 3 bits). If each video image is composed of a single frame (progressive image), it is sufficient to use R(e+f) bits rather than 2R(e+f) bits.

Spatial processing unit 17 is used to identify an area in relative movement in the images from camera 13 and to determnine the speed and oriented direction of the movement. Spatial processing unit 17, in conjunction with delay unit 18, co-operates with a control unit 19 that is controlled by clock 20, which generates clock pulse HP at the pixel frequency. Spatial processing unit 17 receives signals $DP_{ij}$ and $CO_{ij}$ (where i and j correspond to the x and y coordinates of the pixel) from temporal processing unit and processes these signals as discussed below. Whereas temporal processing unit 15 processes pixels within each frame, spatial processing unit 17 processes groupings of pixels within the frames.

FIG. 5 diagrammatically shows the temporal processing of successive corresponding frame sequences $TR_1$, $TR_2$, $TR_3$ and the spatial processing in the these frames of a pixel PI with coordinates x, y, at times $t_1$, $t_2$, and $t_3$. A plane in FIG. 5 corresponds to the spatial processing of a frame, whereas the superposition of frames corresponds to the temporal processing of successive frames.

Signals $DP_{ij}$ and $CO_{ij}$ from temporal processing unit 15 are distributed by spatial processing unit 17 into a first matrix 21 containing a number of rows and columns much smaller than the number of lines L of the frame and the number of pixels M per line. Matrix 21 preferably includes 2l+1 lines along the y axis and 2m+1 columns along the x axis (in Cartesian coordinates), where l and m are small integer numbers. Advantageously, l and m are chosen to be powers of 2, where for example l is equal to $2^a$ and m is equal to $2^b$, a and b being integer numbers of about 2 to 5, for example. To simplify the drawing and the explanation, m will be taken to be equal to l (although it may be different) and $m=l=2^3=8$. In this case, matrix 21 will have 2×8+1=17 rows and 17 columns. FIG. 4 shows a portion of the 17 rows $Y_0, Y_1, \ldots Y_{15}, Y_{16}$, and 17 columns $X_0, X_1, \ldots X_{15}, X_{16}$ which form matrix 21.

Spatial processing unit 17 distributes into l×m matrix 21 the incoming flows of $Dp_{ijt}$ and $CO_{ijt}$ from temporal processing unit 15. It will be appreciated that only a subset of all $DP_{ijt}$, and $CO_{ijt}$ values will be included in matrix 21, since the frame is much larger, having L lines and M pixels per row (e.g., 312.5 lines and 250–800 pixels), depending upon the TV standard used.

In order to distinguish the L×M matrix of the incoming video signal from the l×m matrix 21 of spatial processing unit 17, the indices i and j will be used to represent the coordinates of the former matrix and the indices x and y will be used to represent the coordinates of the latter. At a given instant, a pixel with an instantaneous value $PI_{ijt}$ is characterized at the input of the spatial processing unit 17 by signals $DP_{ijt}$ and $CO_{ijt}$. The (2l+1)×(2m+1) matrix 21 is formed by scanning each of the L×M matrices for DP and CO.

In matrix 21, each pixel is defined by a row number between 0 and 16 (inclusive), for rows $Y_0$. to $Y_{16}$ respectively, and a column number between 0 and 16 (inclusive), for columns $X_0$ to $X_{16}$ respectively, in the case in which l=m=8. In this case, matrix 21 will be a plane of 17×17=289 pixels.

In FIG. 4, elongated horizontal rectangles $Y_0$ to $Y_{16}$ (only four of which have been shown, i.e., $Y_0$, $Y_1$, $Y_{15}$ and $Y_{16}$) and vertical lines X0 to $X_{16}$ (of which only four have been shown, i.e., $X_0$, $X_1$, $X_{15}$ and $X_{16}$) illustrate matrix 21 with 17×17 image points or pixels having indices defined at the intersection of an ordinate row and an abscissa column. For example, the $P_{88}$ is at the intersection of column 8 and row 8 as illustrated in FIG. 4 at position e, which is the center of matrix 21.

In response to the HP and BL signals from clock 20 (FIG. 2), a rate control or sequencing unit 19: i) generates a line sequence signal SL at a frequency equal to the quotient of 13.5 MHZ (for an image with a corresponding number of pixels) divided by the number of columns per frame (for example 400) to delay unit 18, ii) generates a frame signal SC, the frequency of which is equal to the quotient 13.5/400 MHZ divided by the number of rows in the video image, for example 312.5, iii) and outputs the HP clock signal. Blanking signal BL is used to render sequencing unit 19 non-operational during synchronization signals in the input image.

A delay unit 18 carries out the distribution of portions of the L×M matrix into matrix 21. Delay unit 18 receives the DP, CO, and incoming pixel S(PI) signals, and distributes these into matrix 21 using clock signal HP and line sequence and column sequence signals SL and SC.

In order to form matrix 21 from the incoming stream of DP and CO signals, the successive row, $Y_0$ to $Y_{16}$ for the DP and CO signals must be delayed as follows:

row $Y_0$—not delayed;

row $Y_1$—delayed by the duration of a frame line TP;

row $Y_2$ —delayed by 2 TP;

and so on until row $Y_{16}$ —delayed by 16 TP.

The successive delays of the duration of a frame row TP, are carried out in a cascade of sixteen delay circuits $r_1$, $r_2, \ldots r_{16}$ that serve rows $Y_1, Y_2 \ldots Y_{16}$, respectively, row $Y_0$ being served directly by the DP and CO signals without any delay upon arriving from temporal processing unit 15. All delay circuits $r_1, r_2, \ldots r_{16}$, may be built up by a delay line with sixteen outputs, the delay imposed by any section thereof between two successive outputs being constant and equal to TP.

Rate control unit 19 controls the scanning of the entire L×M frame matrix over matrix 21. The circular displacement of pixels in a row of the frame matrix on the 17×17 matrix, for example from $X_0$ to $X_{16}$ on row $Y_0$, is done by a cascade of sixteen shift registers d on each of the 17 rows from $Y_0$ to Y16 (giving a total of 16×17=272 shift registers) placed in each row between two successive pixel positions, namely the register $d_{01}$ between positions $PI_{00}$ and $PI_{01}$ register $d_{02}$ between positions $PI_{01}$, and $PI_{02}$, etc. Each register imposes a delay TS equal to the time difference between two successive pixels in a row or line, using column sequence signal SC. Because rows $l_1, l_2 \ldots l_{17}$ in a frame $TR_1$ (FIG. 1), for S(PI) and for DP and CO, reach delay unit 18 shifted by TP (complete duration of a row) one after the other, and delay unit 18 distributes them with gradually increasing delays of TP onto rows $Y_0, Y_1 \ldots Y_{17}$, these rows display the DP and CO signals at a given time for rows $l_1$, $l_2 \ldots l_{17}$ in the same frame portion. Similarly in a given row, e.g., $l_1$, successive pixel signals $a_{1,1}, a_{12} \ldots$ arrive shifted by TS and shift registers d impose a delay also equal to TS. As a result, the pixels of the DP and CO signals in a given row $Y_0$ to $Y_{16}$ in matrix 21, are contemporary, i.e., they correspond to the same frame portion.

The signals representing the COs and DPs in matrix 21 are available at a given instant on the 16×17=272 outputs of the shift registers, as well as upstream of the registers ahead of the 17 rows, i.e., registers $d_{0,1}, d_{1,1}, \ldots d_{16,1}$, which makes a total of 16×17+17=17×17 outputs for the 17×17 positions $P_{0,0}, P_{01}, \ldots P_{88} \ldots P_{16,16}$.

In order to better understand the process of spatial processing, the system will be described with respect to a small matrix M3 containing 3 rows and 3 columns where the central element of the 9 elements thereof is pixel e with coordinatesx=8, y=8 as illustrated below:

$$a\ b\ c \qquad (M3)$$
$$d\ e\ f$$
$$g\ h\ i$$

In matrix M3, positions a, b, c, d, f, g, h, i around the central pixel e correspond to eight oriented directions relative to the central pixel. The eight directions may be identified using the Freeman code illustrated in FIG. 6, the directions being coded 0 to 7 starting from the x axis, in steps of 45. In the Freeman code, the eight possible oriented directions, may be represented by a 3-bit number since $2^3$32 8.

Considering matrix M3, the 8 direction of the Freeman code are as fallow:

$$3\ 2\ 1$$
$$4\ \underline{e}\ 0$$
$$5\ 6\ 7$$

Returning to matrix 21 having 17×17 pixels, a calculation unit 17a examines at the same time various nested square second matrices centered on e, with dimensions 15×15, 13×13, 11×11, 9×9, 7×7, 5×5 and 3×3, within matrix 21, the 3×3 matrix being the M3 matrix mentioned above. Spatial processing unit 17 determines which matrix is the smallest in which pixels with DP=1 are aligned along a straight line which determines the direction of movement of the aligned pixels.

Figure 7:
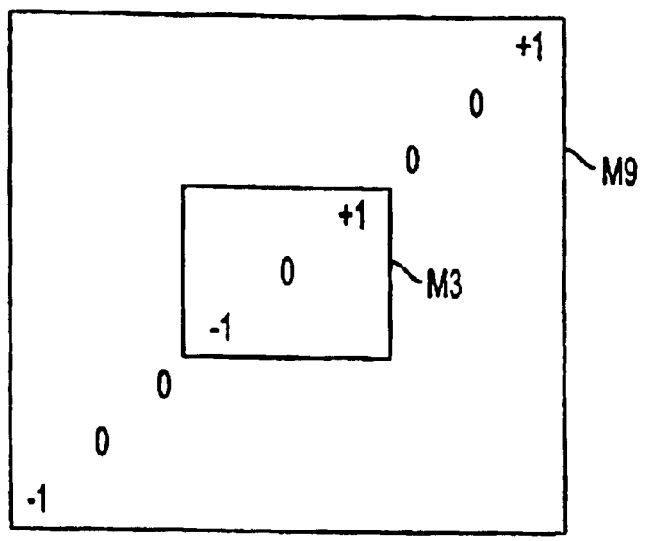
FIG. 7 illustrates nested matrices as processed by the temporal processing unit.

For the aligned pixels in the matrix, the system determines if CO varies on each side of the central position in the direction of alignment, from +a in an oriented direction and −a in the opposite oriented direction, where 1<a<N. For example, if positions g, e, and c of M3 have values −1, 0, +1, then a displacement exists in this matrix from right to left in the (oriented) direction 1 in the Freeman code (FIG. 6). However, positions g, e, and c must at the same time have DP=1. The displacement speed of the pixels in motion is greater when the matrix, among the 3×3 to 15×15 nested matrices, in which CO varies from +1 or −1 between two adjacent positions along a direction is larger. For example, if positions g, e, and c in the 9×9 matrix denoted M9 have values −1, 0, +1 in oriented direction 1, the displacement will be faster than for values −1, 0, +1 in 3×3 matrix M3 (FIG. 7). The smallest matrix for which a line meets the test of DP=1 for the pixels in the line and CO varies on each side of the central position in the direction of alignment, from +a in an oriented direction and −a in the opposite oriented direction, is chosen as the principal line of interest.

Within a given matrix, a greater value of ÅCO indicates slower movement. For example, in the smallest matrix, i.e., the 3×3 matrix, CO=Å2 with DPs=1 determines subpixel movement i.e. one half pixel per image, and CO=Å3, indicates slower movement, i.e. one third of a pixel per image. In order to reduce the calculation power in the system and to simplify the hardware, preferably only those values of CO which are symmetrical relative to the central pixel are considered.

Since CO is represented as a power of 2 in a preferred embodiment, an extended range of speeds may be identified using only a few bits for CO, while still enabling identification of relatively low speeds. Varying speed may be detected because, for example −2, 0, +2 in positions g, e, c in 3×3 matrix M3 indicates a speed half as fast as the speed corresponding to 1, 0, +1 for the same positions in matrix M3.

Two tests are preferably performed on the results to remove uncertainties. The first test chooses the strongest variation, in other words the highest time constant, if there are variations of CO along several directions in one of the nested matrices. The second test arbitrarily chooses one of two (or more) directions along which the variation of CO is identical, for example by choosing the smallest value of the Freeman code, in the instance when identical lines of motion are directed in a single matrix in different directions. This usually arises when the actual direction of displacement is approximately between two successive coded directions in the Freeman code, for example between directions and 2 corresponding to an (oriented) direction that can be denoted 1.5 (FIG. 6) of about 67.5, with the x axis direction (direction 0 in the Freeman code).

The scanning of an entire frame of the digital video signal S preferably occurs in the following sequence. The first group of pixels considered is the first 17 rows or lines of the frame, and the first 17 columns of the frame. Subsequently, still for the first 17 rows of the frame, the matrix is moved column by column from the left of the frame to the right, as shown in FIG. 5, i.e., from portion $TM_1$ at the extreme left, then $TM_2$ offset by one column with respect to $TM_1$, until $TM_M$ (where M is the number of pixels per frame line or row) at the extreme right. Once the first 17 rows have been considered for each column from left to right, the process is repeated for rows 2 to 18 in the frame. This process continues, shifting down one row at a time until the last group of lines at the bottom of the frame, i.e., lines L–16 . . . L (where L is the number of lines per frame) are considered.

Spatial processing unit 17 generates the following output signals for each pixel: i) a signal V representing the displacement speed for the pixel, based upon the amplitude of the maximum variation of CO surrounding the pixel, the value of which may be, for example, represented by an integer in the range 0–7 if the speed is in the form of a power of 2, and therefore may be stored in 3 bits, ii) a signal DI representing the direction of displacement of the pixel, which is calculated from the direction of maximum variation, the value of DI being also preferably represented by an integer in the range 0–7 corresponding to the Freeman code, stored in 3 bits, iii) a binary validation signal VL which indicates whether the result of the speed and oriented direction is valid, in order to be able to distinguish a valid output with V=0 and DI=0, from the lack of an output due to an incident, this signal being 1 for a valid output or 0 for an invalid output, iv) a time constant signal CO, stored in 3 bits, for example, and v) a delayed video signal SR consisting of the input video signal S delayed in the delay unit 18 by 16 consecutive line durations TR and therefore by the duration of the distribution of the signal S in the 17×17 matrix 21, in order to obtain a video signal timed to matrix 21, which may be displayed on a television set or monitor. Also output are the clock signal HP, line sequence signal SL and column sequence signal SC from control unit 19.

Figure 8:
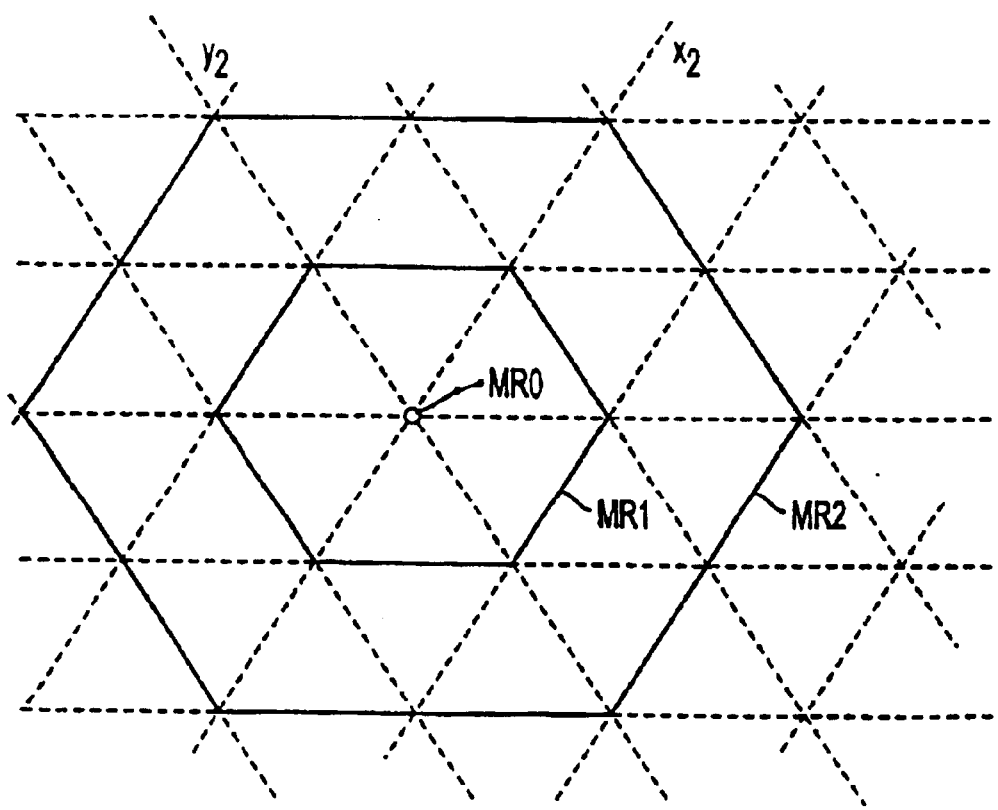
FIG. 8 illustrates hexagonal matrices as processed by the temporal processing unit.

Nested hexagonal matrices (FIG. 8) or an inverted L-shaped matrix (FIG. 9) may be substituted for the nested rectangular matrices in FIGS. 4 and 7. In the case shown in FIG. 8, the nested matrices (in which only the most central matrices MRI and MR2 have been shown) are all centered on point MR0 which corresponds to the central point of matrices M3, M9 in FIG. 7. The advantage of a hexagonal matrix system is that it allows the use of oblique coordinate axes $x_a$, $y_a$, and a breakdown into triangles with identical sides, to carry out an isotropic speed calculation.

The matrix in FIG. 9 is composed of a single row ($L_u$) and a single column ($C_u$) starting from the central position $MR_u$ in which the two signals DP and CO respectively are equal to "1" for DP and increase or decrease by one unit for CO, if movement occurs.

If movement is in the direction of the x coordinate, the CO signal is identical in all positions (boxes) in column $C_u$, and the binary signal DP is equal to 1 in all positions in row $L_u$, from the origin $MR_u$, with the value $CO_u$, up to the position in which CO is equal to $CO_u+1$ or –1 inclusive. If movement is in the direction of the y coordinate, the CO signal is identical in all positions (boxes) in row $L_u$, and the binary signal DP is equal to 1 in all positions in column $C_u$, from the origin $MR_u$, with the value $CO_u$, up to the position in which CO is equal to $CO_u$, +1 or –1 inclusive. If movement is oblique relative to the x and y coordinates, the binary signal DP is equal to 1 and CO is equal to $CO_u$ in positions (boxes) of $L_u$ and in positions (boxes) of $C_u$, the slope being determined by the perpendicular to the line passing through the two positions in which the signal $CO_u$ changes by the value of one unit, the DP signal always being equal to 1.

FIG. 9 shows the case in which DP=1 and $CO_u$ changes value by one unit in the two specific positions $L_{u3}$ and $C_{u5}$ and indicates the corresponding slope $P_p$. In all cases, the displacement speed is a function of the position in which CO changes value by one unit. If CO changes by one unit in $L_u$ or $C_u$ only, it corresponds to the value of the CO variation position. If CO changes by one unit in a position in $L_u$ and in a position in $C_u$, the speed is proportional to the distance between $MR_u$ and $E_u$ (intersection of the line perpendicular to $C_u$–$L_u$ passing through $MR_u$).

FIG. 10 shows an imaging device with sensors located at the intersections of concentric lines c and radial lines d that correspond to the rows and columns of a rectangular matrix imaging device. The operation of such an imaging device is controlled by a circular scanning sequencer. In this embodiment, angular sector shaped n x n matrices MC are formed, (a 3×3 matrix MC3 and a 5×5 matrix MC5 are shown) and except for sequencing differences, the matrices are processed identical to the square matrix embodiments discussed above.

As shown in FIGS. 11–16, spatial and temporal processing unit 11 is used in connection with a histogram processor 22a for identifying objects within the input signal based upon user specified criteria for identifying such objects. A bus Z-$Z_1$ (See FIGS. 2, 11 and 12) transfers the output signals of spatial and temporal processing unit II to histogram processor 22a. Histogram processor 22a generates composite output signal ZH which contains information on the areas in relative movement in the scene.

Figure 12:
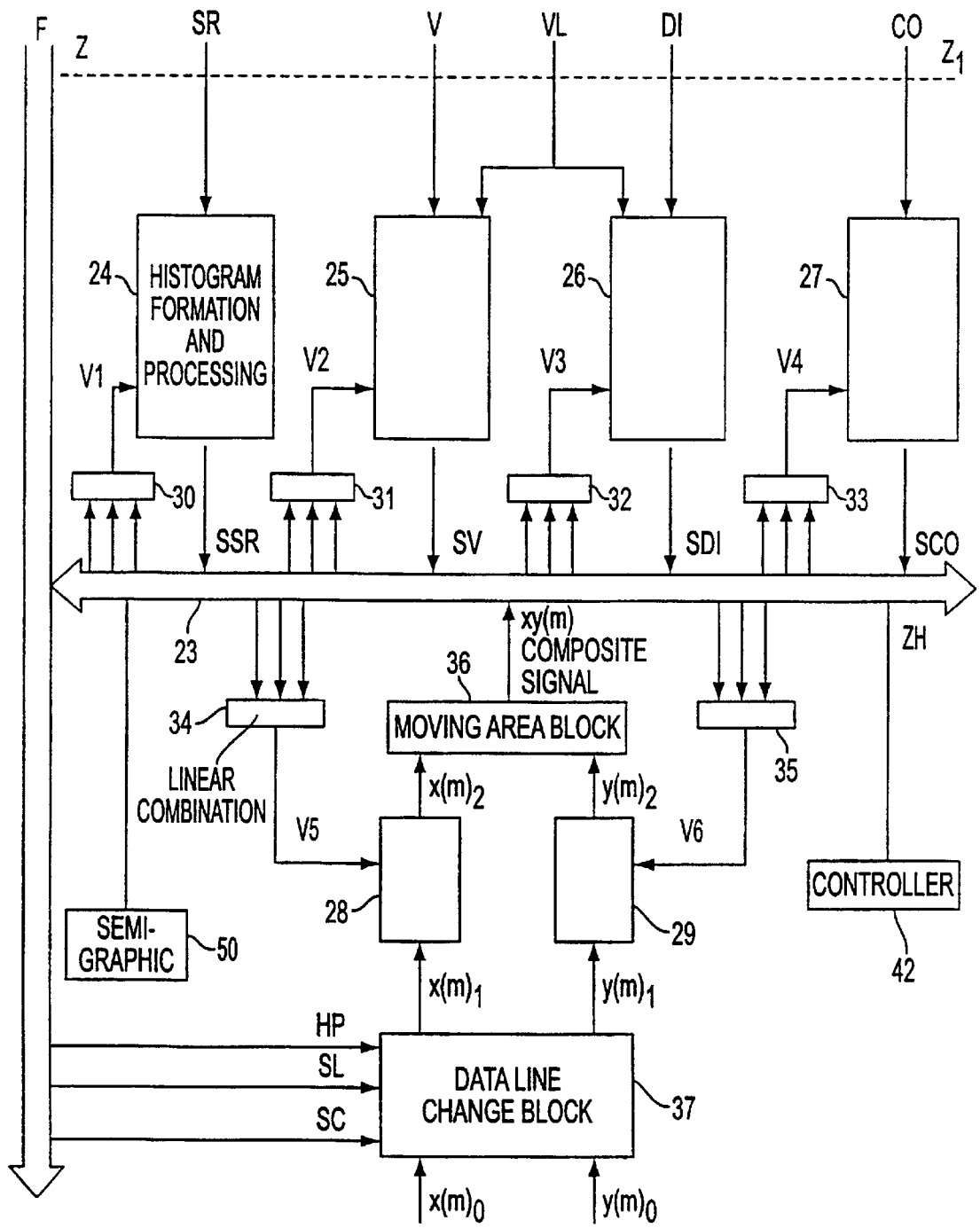
FIG. 12 is a block diagram showing the interrelationship between the various histogram formation units.

Referring to FIG. 12, histogram processor 22a includes a bus 23 for communicating signals between the various components thereof, for receiving input commands from a controller 42 and for transmitting output signals to controller 42. Histogram formation and processing blocks 24–29 receive the various input signals, i.e., delayed digital video signal SR, speed V, oriented directions (in Freeman code) DI, time constant CO, first axis x(m) and second axis y(m), which are discussed in detail below. The function of each histogram formation block is to enable a histogram to be formed for the domain associated with that block. For example, histogram formation block 24 receives the delayed digital video signal SR and enables a histogram to be formed for the luminance values of the video signal. Since the luminance of the signal will generally be represented by a number in the range of 0–255, histogram formation block 24 is preferably a memory addressable with 8 bits, with each memory location having a sufficient number of bits to correspond to the number of pixels in a frame.

Histogram formation block 25 receives speed signal V and enables a histogram to be formed for the various speeds present in a frame. In a preferred embodiment, the speed is an integer in the range 0–7. Histogram formation block 25 is then preferably a memory addressable with 3 bits, with each memory location having a sufficient number of bits to correspond to the number of pixels in a frame.

Histogram formation block 26 receives oriented direction signal DI and enables a histogram to be formed for the oriented directions present in a frame. In a preferred embodiment, the oriented direction is an integer in the range 0–7, corresponding to the Freeman code. Histogram formation block 26 is then preferably a memory addressable with 3 bits, with each memory location having a sufficient number of bits to correspond to the number of pixels in a frame.

Histogram formation block 27 receives time constant signal CO and enables a histogram to be formed for the time constants of the pixels in a frame. In a preferred embodiment, the time constant is an integer in the range 0–7. Histogram formation block 27 is then preferably a memory addressable with 3 bits, with each memory location having a sufficient number of bits to correspond to the number of pixels in a frame.

Histogram formation blocks 28 and 29 receive the x and y positions respectively of pixels for which a histogram is to be formed, and form histograms for such pixels, as discussed in greater detail below. Histogram formation block 28 is preferably addressable with the number of bits corresponding to the number of pixels in a line, with each memory location having a sufficient number of bits to correspond to the number of lines in a frame, and histogram formation block 29 is preferably addressable with the number of bits corresponding to the number of lines in a frame, with each memory location having a sufficient number of bits to correspond to the number of pixels in a line.

Figure 14:
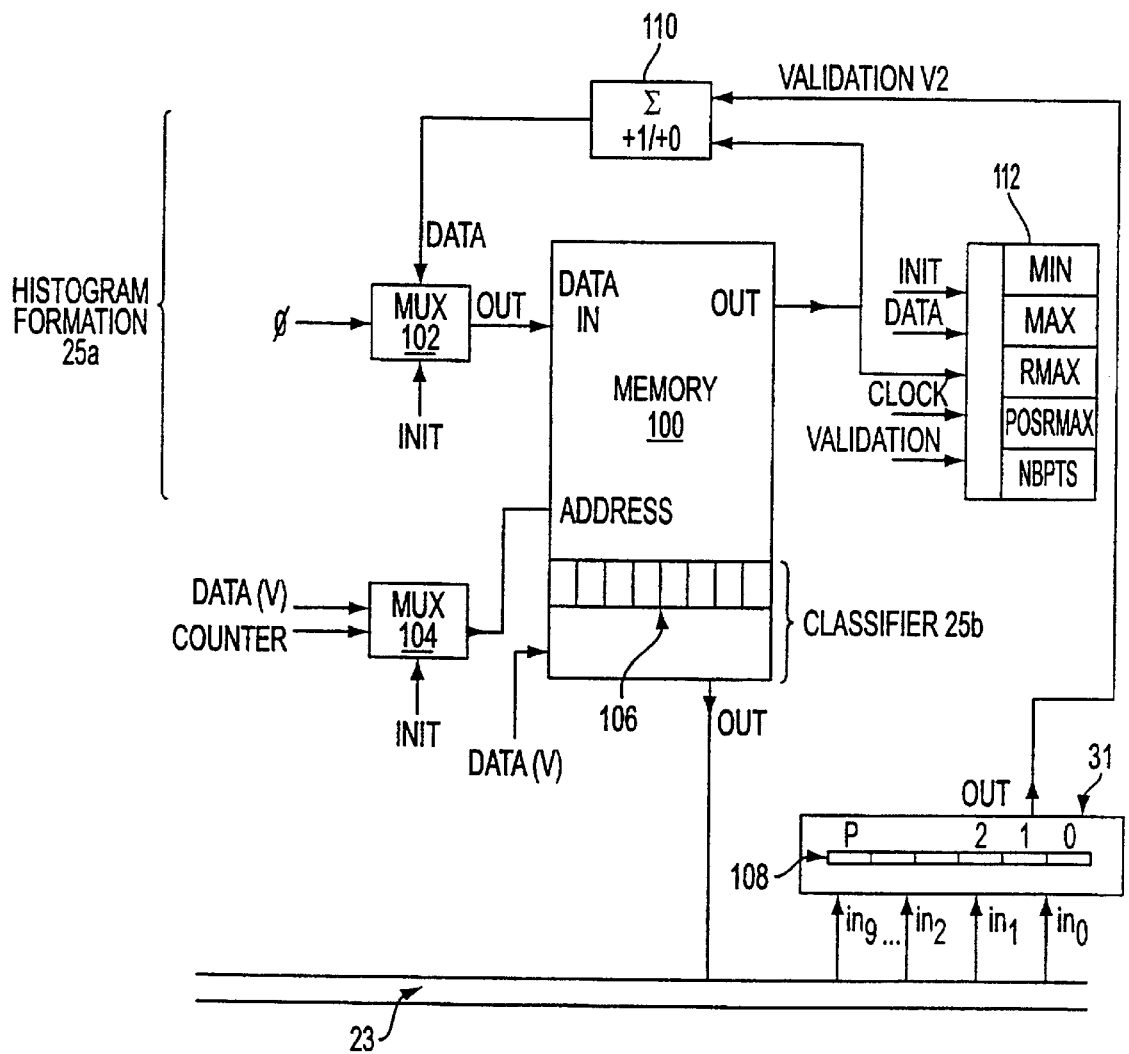
FIG. 14 is a block diagram of an individual histogram formation unit.

Referring to FIGS. 12 and 14, each of the histogram formation blocks 24–29 has an associated validation block 30–35 respectively, which generates a validation signal V1–V6 respectively. In general, each of the histogram formation blocks 24–29 is identical to the others and functions in the same manner. For simplicity, the invention will be described with respect to the operation of histogram formation block 25, it being appreciated that the remaining histogram formation blocks operate in a like manner. Histogram formation block 25 includes a histogram forming portion 25*a*, which forms the histogram for that block, and a classifier 25*b*, for selecting the criteria of pixels for which the histogram is to be formed. Histogram forming portion 25*a* and classifier 25*b* operate under the control of computer software in an integrated circuit (not shown), to extract certain limits of the histograms generated by the histogram formation block, and to control operation of the various components of the histogram formation units.

Referring to FIG. 14, histogram forming portion 25*a* includes a memory 100, which is preferably a conventional digital memory. In the case of histogram formation block 25 which forms a histogram of speed, memory 100 is sized to have addresses 0–7, each of which may store up to the number of pixels in an image. Between frames, memory 100 is initiated, i.e., cleared of all memory, by setting init=1 in multiplexors 102 and 104. This has the effect, with respect to multiplexor 102 of selecting the "0" input, which is output to the Data In line of memory 100. At the same time, setting init=1 causes multiplexor 104 to select the Counter input, which is output to the Address line of memory 100. The Counter input is connected to a counter (not shown) that counts through all of the addresses for memory 100, in this case $0 \leq address \leq 7$. This has the effect of placing a zero in all memory addresses of memory 100. Memory 100 is preferably cleared during the blanking interval between each frame. After memory 100 is cleared, the init line is set to zero, which in the case of multiplexor 102 results in the content of the Data line being sent to memory 100, and in the case of multiplexor 104 results in the data from spatial processing unit 117, i.e., the V data, being sent to the Address line of memory 100.

Classifier 25*b* enables only data having selected classification criteria to be considered further, meaning to possibly be included in the histograms formed by histogram formation blocks 24–29. For example, with respect , to speed, which is preferably a value in the range of 0–7, classifier 25*b* may be set to consider only data within a particular speed category or categories, e.g., speed 1, speeds 3 or 5, speed 3–6, etc. Classifier 25*b* includes a register 106 that enables the classification criteria to be set by the user, or by a separate computer program. By way of example, register 106 will include, in the case of speed, eight registers numbered 0–7. By setting a register to "1", e.g., register number 2, only data that meets the criteria of the selected class, e.g., speed 2, will result in a classification output of "1". Expressed mathematically, for any given register in which R(k)=b, where k is the register number and b is the boolean value stored in the register:

$$Output=R(data(V))$$

So for a data point V of magnitude 2, the output of classifier 25*b* will be "1" only if R(2)=1. The classifier associated with histogram formation block 24 preferably has 256 registers, one register for each possible luminance value of the image. The classifier associated with histogram formation block 26 preferably has 8 registers, one register for each possible direction value. The classifier associated with histogram formation block 27 preferably has 8 registers, one register for each possible value of CO. The classifier associated with histogram formation block 28 preferably has the same number of registers as the number of pixels per line. Finally, the classifier associated with histogram formation block 29 preferably has the same number of registers as the number of fines per frame. The output of each classifier is communicated to each of the validation blocks 30–35 via bus 23, in the case of histogram formation blocks 28 and 29, through combination unit 36, which will be discussed further below.

Validation units 30–35 receive the classification information in parallel from all classification units in histogram formation blocks 24–29. Each validation unit generates a validation signal which is communicated to its associated histogram formation block 24–29. The validation signal determines, for each incoming pixel, whether the histogram formation block will utilize that pixel in forming its histogram. Referring again to FIG. 14, which shows histogram formation block 25, validation unit 31 includes a register block 108 having a register associated with each histogram formation block, or more generally, a register associated with each data domain that the system is capable of processing, in this case, luminance, speed, direction, CO, and x and y position. The content of each register in register block 108 is a binary value that may be set by a user or by a computer controller. Each validation unit receive via bus 23 the output of each of the classifiers, in this case numbered 0 . . . p, keeping in mind that for any data domain, e.g., speed, the output of the classifier for that data domain will only be "1" if the particular data point being considered is in the class of the registers set to "1" in the classifier for that data domain. The validation signal from each validation unit will only be "1" if for each register in the validation unit that is set to "1", an input of "1" is received from the classifier for the domain of that register. This may be expressed as follows:

$$out=(\overline{in}_0+Reg_0) \cdot (\overline{in}_1+Reg_1) \ldots (\overline{in}_n+Reg_n)(in_0+in_1+ \ldots in_n)$$

where $Reg_0$ is the register in the validation unit associated with input $in_0$. Thus, using the classifiers in combination with validation units 30–35, the system may select for processing only data points in any selected classes within any selected domains. For example, the system may be used to detect only data points having speed 2, direction 4, and luminance 125 by setting each of the following registers to "1": the registers in the validation units for speed, direction, and luminance, register 2 in the speed classifier, register 4 in the direction classifier, and register 125 in the luminance classifier. In order to form those pixels into a block, the registers in the validation units for the x and y directions would be set to "1" as well.

Referring again to FIG. 14, validation signal V2 is updated on a pixel-by-pixel basis. If, for a particular pixel, validation signal V2 is "1", adder 110 increments the output of memory 100 by one. If, for a particular pixel, validation signal V2 is "0", adder 100 does not increment the output of memory. In any case, the output of adder 100 is stored in memory 100 at the address corresponding to the pixel being considered. For example, assuming that memory 100 is used to form a histogram of speed, which may be categorized as speeds 0–7, and where memory 100 will include 0–7 corresponding memory locations, if a pixel with speed 6 is received, the address input to multiplexor 104 through the data line will be 6. Assuming that validation signal V2 is "1", the content in memory at location 6 will be incremented. Over the course of an image, memory 100 will contain a histogram of the pixels for the image in the category associated with the memory. If, for a particular pixel, validation signal V2 is "0" because that pixel is not in a category for which pixels are to be counted (e g., because that pixel does not have the correct direction, speed, or luminance), that pixel will not be used in forming the histogram.

For the histogram formed in memory 100, key characteristics for that histogram are simultaneously computed in a unit 112. Referring to FIG. 14, unit 112 includes memories for each of the key characteristics, which include the minimum (MIN) of the histogram, the maximum (MAX) of the histogram, the number of points (NBPTS) in the histogram, the position (POSRMAX) of the maximum of the histogram, and the number of points (RMAX) at the maximum of the histogram. These characteristics are determined in parallel with the formation of the histogram as follows:

For each pixel with a validation signal V2 of "1":
  (a) if the data value of the pixel<MIN (which is initially set to the maximum possible value of the histogram), then write data value in MIN;
  (b) if the data value of the pixel>MAX (which is initially set to the minimum possible value of the histogram), then write data value in MAX;
  (c) if the content of memory 100 at the address of the data value of the pixel>RMAX (which is initially set to the minimum possible value of the histogram), then i) write data value in POSRMAX and ii) write the memory output in RMAX.
  (d) increment NBPTS (which is initially set to zero).

At the completion of the formation of the histogram in memory 100 at the end of each femme, unit 112 will contain important data characterizing the histogram. The histogram in each memory 100, and the characteristics of the histogram in units 112 are read during the scanning spot of each frame by controller 42, and the memories 100 are cleared and units 112 are re-initialized for processing the next frame.

Figure 17:
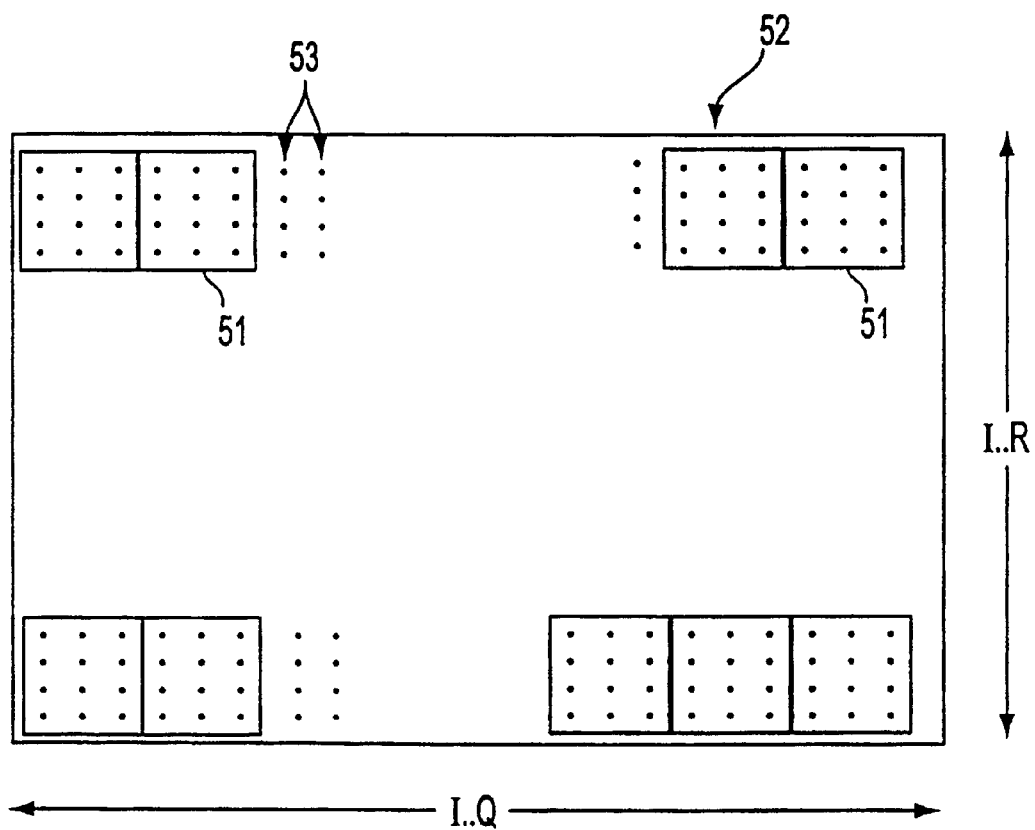
FIG. 17 illustrates the use of semi-graphic sub-matrices to selected desired areas of an image.

The system of the invention includes a semi-graphic masking function to select pixels to be considered by the system. FIG. 17 shows a typical image 52 consisting of pixels 53 arranged in a Q×R matrix, which is divided into sub-matrices 51 each having a dimension of s×t, wherein each s×t sub-matrix includes s×t number of pixels of the image. Each sub-matrix shown in FIG. 17 is a 3×4 matrix. In a preferred embodiment, s=9 and t=12, although any appropriate sub-matrix size may be used, if desired, including 1×1. Referring to FIG. 12, histogram processor 22a includes a semi-graphic memory 50, which includes a one-bit memory location corresponding to each s×t matrix. For any given sub-matrix 51, the corresponding bit in memory 50 may be set to "0", which has the effect of ignoring all pixels in such sub-matrix 51, or may be set to "1" in which case all pixels in such sub-matrix 51 will be considered in forming histograms. Thus, by using semi-graphic memory 50, it is possible to limit those areas of the image to be considered during histogram formation. For example, when an image of a road taken by a camera facing forward on a vehicle is used to detect the lanes of the road, the pixel information of the road at the farthest distances from the camera generally does not contain useful information. Accordingly, in such an application, the semi-graphic memory 50 is used to mask off the distant portions of the road by setting semi-graphic memory 50 to ignore such pixels. Alternatively, the portion of the road to be ignored may be masked by setting the system to track pixels only within a detection box that excludes the undesired area of the screen, as discussed below.

In operation, for any pixel under consideration, an AND operation is run on the validation signal for such pixel and the content of semi-graphic memory 50 for the sub-matrix in which that pixel is located. If the content of semi-graphic memory 50 for the sub-matrix in which that pixel is located contains "0", the AND operation will yield a "0" and the pixel will be ignored, otherwise the pixel will be considered in the usual manner. It is foreseen that the AND operation may be run on other than the validation signal, with the same resultant functionality. Also, it is foreseen that memory 50 may be a frame size memory, with each pixel being independently selectable in the semi-graphic memory. This would enable any desired pixels of the image to be considered or ignored as desired. Semi-graphic memory 50 is set by controller 42 via data bus 23.

Figure 16:
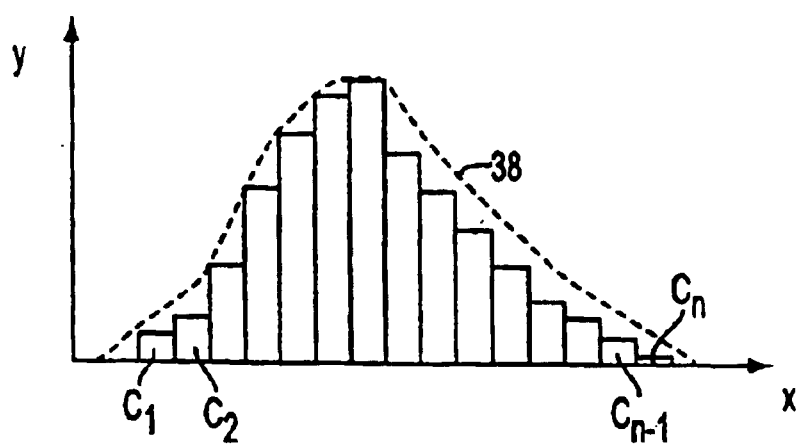
FIG. 16 illustrates a one-dimensional histogram.

FIG. 16 shows an example of the successive classes $C_1$, $C_2 \ldots C_{n-1}$, $C_n$, each representing a particular velocity, for a hypothetical velocity histogram, with their being categorization for up to 16 velocities (15 are shown) in this example. Also shown is envelope 38, which is a smoothed representation of the histogram.

Figure 13:
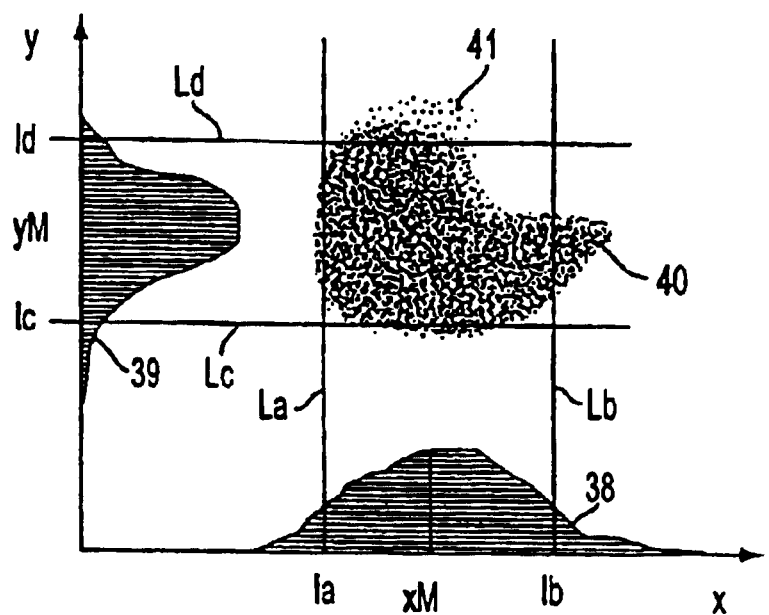
FIG. 13 shows the formation of a two-dimensional histogram of a moving area from two one-dimensional histograms.

In order to locate the position of an object having user specified criteria within the image, histogram blocks 28 and 29 are used to generate histograms for the x and y positions of pixels with the selected criteria. These are shown in FIG. 13 as histograms along the x and y coordinates. These x and y data are output to moving area formation block 36 which combines the abscissa and ordinate information $x(m)_2$ and $y(m)_2$ respectively into a composite signal xy(m) that is output onto bus 23. A sample composite histogram 40 is shown in FIG. 13. The various histograms and composite signal xy(m) that are output to bus 23 are used to determine if there is a moving area in the image, to localize this area, and/or to determine its speed and oriented direction. Because the area in relative movement may be in an observation plane along directions x and y which are not necessarily orthogonal, as discussed below with respect to FIG. 18, a data change block 37 (FIG. 12) may be used to convert the x and y data to orthogonal coordinates. Data change block 37 receives orientation signals $x(m)_1$ and $y(m)_0$ for $x(m)o$ and $y(m)_0$ axes, as well as pixel clock signals HP, line sequence and column sequence signals SL and SC (these three signals being grouped together in bundle F in FIGS. 2, 4, and 11) and generates the orthogonal $x(m)_1$ and $y(m)_1$ signals that are output to a histogram formation blocks 28 and 29 respectively.

In order to process pixels only within a user defined area, the x-direction histogram formation unit 28 may be programmed to process pixels only in a class of pixels defined by boundaries, i.e. XMIN and XMAX. This is accomplished by setting the XMIN and XMAX values in a user-programmable memory in x-direction histogram formation unit 28 or in linear combination units 30–35. Any pixels outside of this class will not be processed. Similarly, y-direction histogram formation unit 29 may be set to process pixels only in a class of pixels defined by boundaries YMIN and YMAX. This is accomplished by setting the YMIN and YMAX values in a user-programmable memory in y-direction histogram formation unit 29 or in linear combination units 30–35. Thus, the system can process pixels only in a defined rectangle by setting the XMIN and XMAX, and YMIN and YMAX values as desired. Of course, the classification criteria and validation criteria from the other histogram formation units may be set in order to form histograms of only selected classes of pixels in selected domains within the selected rectangular area. The XMIN and XMAX memory locations have a sufficient number of bits to represent the maximum number of pixels in the x dimension of the image under consideration, and the YMIN and YMAX memory locations have a sufficient number of bits to represent the maximum number of pixels in the y dimension of the image under consideration. As discussed further below, the x and y axes may be rotated in order to create histograms of projections along the rotated axes. In a preferred embodiment, the XMIN, XMAX, YMIN and YMAX memory locations have a sufficient number of bits to represent the maximum number of pixels along the diagonal of the image under consideration (the distance from "Origin" to "Stop" in FIG. 15). In this way, the system may be used to search within a user-defined rectangle along a user-defined rotated axis system.

In order to process pixels only within a user defined area, the x-direction histogram formation unit 28 may be programmed to process pixels only in a class of pixels defined by boundaries, i.e. XMIN and XMAX. This is accomplished by setting the XMIN and XMAX values in a user-programmable memory in x-direction histogram formation unit 28 or in linear combination units 30–35. Any pixels outside of this class will not be processed. Similarly, y-direction histogram formation unit 29 may be set to process pixels only in a class of pixels defined by boundaries YMIN and YMAX. This is accomplished by setting the YMIN and YMAX values in a user-programmable memory in y-direction histogram formation unit 29 or in linear combination units 30–35. Thus, the system can process pixels only in a defined rectangle by setting the XMIN and XMAX, and YMIN and YMAX values as desired. Of course, the classification criteria and validation criteria from the other histogram formation units may be set in order to form histograms of only selected classes of pixels in selected domains within the selected rectangular area. The XMIN and XMAX memory locations have a sufficient number of bits to represent the maximum number of pixels in the x dimension of the image under consideration, and the YMIN and YMAX memory locations have a sufficient number of bits to represent the maximum number of pixels in the y dimension of the image under consideration. As discussed further below, the x and y axes may be rotated in order to create histograms of projections along the rotated axes. In a preferred embodiment, the XMIN, XMAX, YMIN and YMAX memory locations have a sufficient number of bits to represent the maximum number of pixels along the diagonal of the image under consideration (the distance from "Origin" to "Stop" in FIG. 15). In this way, the system may be used to search within a user-defined rectangle along a user-defined rotated axis system.

In order for a pixel PI(a,b) to be considered in the formation of x and y direction histograms, whether on the orthogonal coordinate axes or along rotated axes, the conditions XMIN<a<XMAX and YMIN<b<YMAX must be satisfied. The output of these tests may be ANDed with the validation signal so that if the conditions are not satisfied, a logical "0" is ANDed with the validation signal for the pixel under consideration, thereby avoiding consideration of the pixel in the formation of x and y direction histograms.

FIG. 13 diagrammatically represents the envelopes of histograms 38 and 39, respectively in x and y coordinates, for velocity data. In this example, $x_m$ and $y_M$ represent the x and y coordinates of the maxima of the two histograms 38 and 39, whereas $l_a$ and $l_b$ for the x axis and $l_c$ and $l_d$ for the y axis represent the limits of the range of significant or interesting speeds, $l_a$ and $l_c$ being the lower limits and $l_b$ and $l_d$ being the upper limits of the significant portions of the histograms. Limits $l_a$, $l_b$, $l_c$ and $l_d$ may be set by the user or by an application program using the system, may be set as a ratio of the maximum of the histogram, e.g., $x_M/2$, or may be set as otherwise desired for the particular application.

The vertical lines $L_a$ and $L_b$ of abscissas $l_a$ and $l_b$ and the horizontal lines $L_c$ and $L_d$ of ordinals $l_c$ and $l_d$ form a rectangle that surrounds the cross hatched area 40 of significant speeds (for all x and y directions). A few smaller areas 41 with longer speeds, exist close to the main area 40, and are typically ignored. In this example, all that is necessary to characterize the area with the largest variation of the parameter for the histogram, the speed V in this particular case, is to identify the coordinates of the limits $l_a$, $l_b$, $l_c$ and $l_d$ and the maxima $X_M$ and $Y_M$, which may be readily derived for each histogram from memory 100, the data in units 112, and the xy(m) data block.

Thus, the system of the invention generates in real time, histograms of each of the parameters being detected. Assuming that it were desired to identify an object with a speed of "2" and a direction of "4", the validation units for speed and direction would be set to "1", and the classifiers for speed "2" and direction "4" would be set to "1". In addition, since it is desired to locate the object(s) with this speed and direction on the video image, the validation signals for histogram formation blocks 28 and 29, which correspond to the x and y coordinates, would be set to "1" as well. In this way, histogram formation blocks 28 and 29 would form histograms of only the pixels with the selected speed and direction, in real-time. Using the information in the histogram, and especially POSRMAX, the object with the greatest number of pixels at the selected speed and direction could be identified on the video image in real-time. More generally, the histogram formation blocks can localize objects in real-time meeting user-selected criteria, and may produce an output signal if an object is detected. Alternatively, the information may be transmitted, e.g., by wire, optical fiber or radio relay for remote applications, to a control unit, such as unit 10a in FIG. 1, which may be near or remote from spatial and temporal processing unit 11.

Figure 15A:
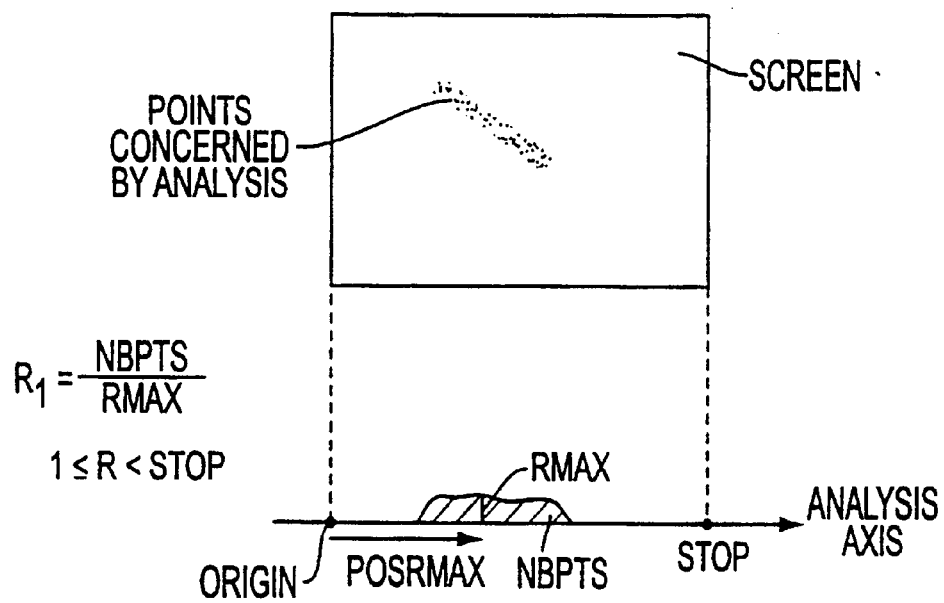
FIGS. 15A and 15B illustrate the use of a histogram formation unit to find the orientation of a line relative to an analysis axis.
Figure 15B:
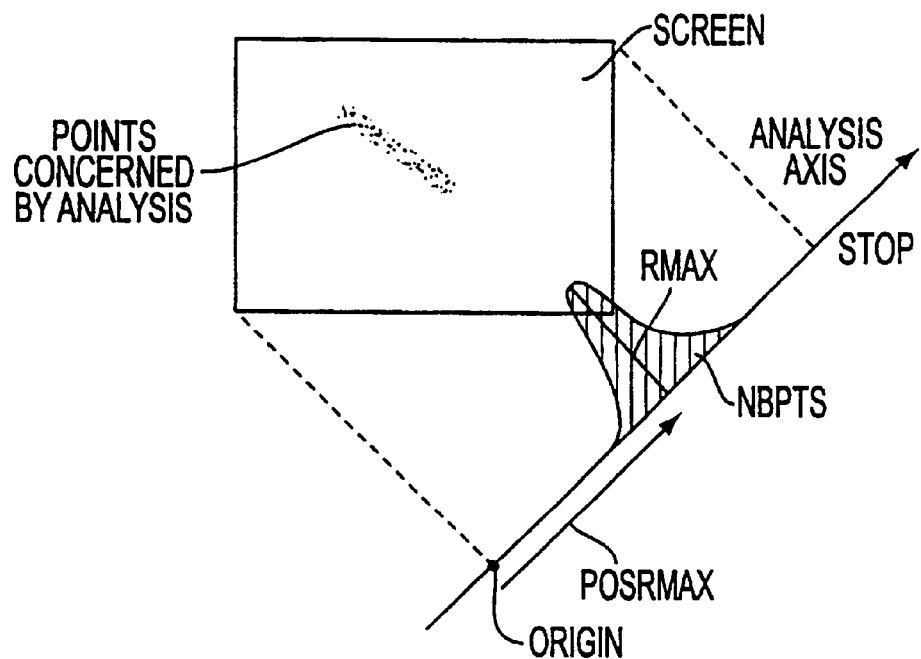

While the system of the invention has been described with respect to formation of histograms using an orthogonal coordinate system defined by the orizontal and vertical axes of the video image, the system may be used to from histogram using non-orthogonal axes that are user-defined. FIGS. 15A and 15B show a method of using rotation of the analysis axis to determine tthe orientation of certain points in an image, a method which may be used, for example to detect lines. In a preferred embodiment, the x-axis may be rotated in up to 16 different directions (180°/16), and the y-axis may be independently rotated by up to 16 different directions. Rotation of the axes is accomplished using data line change block 37 which receives as an input the user-defined axes of rotation for each of the x and y axes, and which performs a Hough transform to convert the x and y cordinte values under consideration into the rotated cordinate axis system for consideration by by the x and y histogram formation units 28 and 29. The operation of conversion betweeen cordinate system using a Hough transform is known in the art. Thus, the user may select rotation the x-coordinate system in up to 16 different directions, and may independently rotate the y-coordinate system in up to 16 different directions. Using the rotated coordinate systems, the system may perform the functionally describe above, including searching within user-defined rectangles (on the rotated axes), forming histograms on the rotated axes, and searching using velocity, direction, etc.

As discussed above, each histogram formation unit calculates the following values for its respective histogram.

MIN, MAX, NBPTS, RMAX, POSRMAX

Given that these values are calculated in real-time, the use of these values allows the system to rapidly identify lines on an image. While this may be accomplished in a number of different ways, one of the easier methods is to calculate R, where R=NBPTS/RMAX, i.e., the ratio of the number of points in the histogram to the number of points in the maximal line. The smaller this ratio, i.e., the closer R approaches 1, the more perpendicularly aligned the data points under consideration are with the scanning axis.

FIG. 15A shows a histogram of certain points under consideration, where the histogram is taken along the x-axis, i.e., projected down onto the x-axis. In this example, the ratio R, while not calculated, is high, and contains little information about the orientation of the points under consideration. As the x-axis is rotated, the ratio R decreases, until, as shown in FIG. 15B, at approximately 45° the ratio R would reach a minimum. This indicates that the points under consideration are most closely aligned perpendicular to the 45° x=axis. In operation, on successive frames, or on the same frame if multiple x-direction histogram formation units are available, it is advantageous to calculate R at different angles, e.g., 33.75° and 57.25° (assuming the axes are limited to 16 degrees of rotation), in order to constantly ensure that R is at a minimum. For applications in which it is desirable to detect lines, and assuming the availability of 16 x-direction histogram formation units, it is advantageous to carry out the calculation of R simultaneously along all possible axes to determine the angle with the minimum R to determine the direction of orientation of the line. Because the x and y axes may be rotated independently, the x and y histogram formation units are capable of simultaneously independently detecting lines, such as each side line of a road, in the same manner.

As discussed above, the system of the invention may be used to search for objects within a bounded area defined by XMIN, XMAX, YMIN and YMAX. Because a moving object may leave the bounded area the system preferably includes an anticipation function which enables XMIN, XMAX, YMIN and YMAX to be automatically modified by the system to compensate for the speed and direction of the target. This is accomplished by determining values for O-MVT, corresponding to orientation (direction) of movement of the target within the bounded area using the direction histogram, and I-MVT, corresponding to the intensity (velocity) of movement. Using these parameters, controller 42 may modify the values of XMIN, XMAX, YMIN and YMAX on a frame-by-frame basis to ensure that the target remains in the bounded box being searched. These parameters also enable the system to determine when a moving object, e.g., a line, that is being tracked based upon its axis of rotation, will be changing its axis of orientation, and enable the system to anticipate a new orientation axis in order to maintain a minimized value of R.

Referring to FIG. 12, a controller 42, which is preferably a conventional microprocessor based controller, is used to control the various elements of the system and to enable user input of commands and controls, such as with a computer mouse and keyboard (not shown), or other input device. Referring to FIG. 11, components 11 and 22a, and controller 42, are preferably formed on a single integrated circuit. Controller 42 is in communication with data bus 23, which allows controller 42 to run a program to control various parameters that may be set in the system and to analyze the results. In order to select the criteria of pixels to be tracked, controller 42 may also directly control the following: i) content of each register in classifiers 25b, ii) the content of each register in validation units 30–35; iii) the content of XMIN, XMAX, YMIN and YMAX, iv) the orientation angle of each of the x and y axes, and v) semi-graphic memory 50. Controller 42 may also retrieve i) the content of each memory 100 and ii) the content of registers 112, in order to analyze the results of the histogram formation process. In addition, in general controller 42 may access and control all data and parameters used in the system.

The system of the invention may be used to detect the driver of a vehicle falling asleep and to generate an alarm upon detection thereof. While numerous embodiments of the invention will be described, in general the system receives an image of the driver from a camera or the like and processes the image to detect one or more criteria of the eyes of the driver to determine when the driver's eyes are open and when they are closed. As discussed above, a wide-awake person generally blinks at relatively regular intervals of about 100 to 200 ms. When a person becomes drowsy, the length of each eye blink increases to approximately 500 to 800 ms, with the intervals between blinks being becoming longer and variable. Using the information on the opening and closing of the driver's eyes, the system measures the duration of each blink and/or the intervals between blinks to determine when the driver is falling asleep. This is possible because the video signal coming from the sensor in use, e.g., sensor 310 of FIG. 21, preferably generates 50 or 60 frames per second, i.e., a frame every 20 ms or 16.66 ms respectively. This makes it possible for the system, which processes each image in real time, to distinguish between blink lengths of 100 to 200 ms for an awake person from blink lengths of 500 to 800 ms for a drowsy person, i.e., a blink length of 5 to 10 frames for an awake person or a blink length of 25 to 40 frames for a drowsy person, in the case of a 50 frames per second video signal.

The system of the invention utilizes a video camera or other sensor to receive images of the driver T in order to detect when the driver is falling asleep. While various methods of positioning the sensor shall be described, the sensor may generally be positioned by any means and in any location that permits acquisition of a continuous image of the face of the driver when seated in the driver's seat. Thus, it is foreseen that sensor 310 may be mounted to the vehicle or on the vehicle in any appropriate location, such as in or on the vehicle dashboard, steering wheel, door, rear-view mirror, ceiling, etc., to enable sensor 310 to view the face of the driver. An appropriate lens may be mounted on the sensor 310 to give the sensor a wider view if required to see drivers of different sizes.

Figure 18:
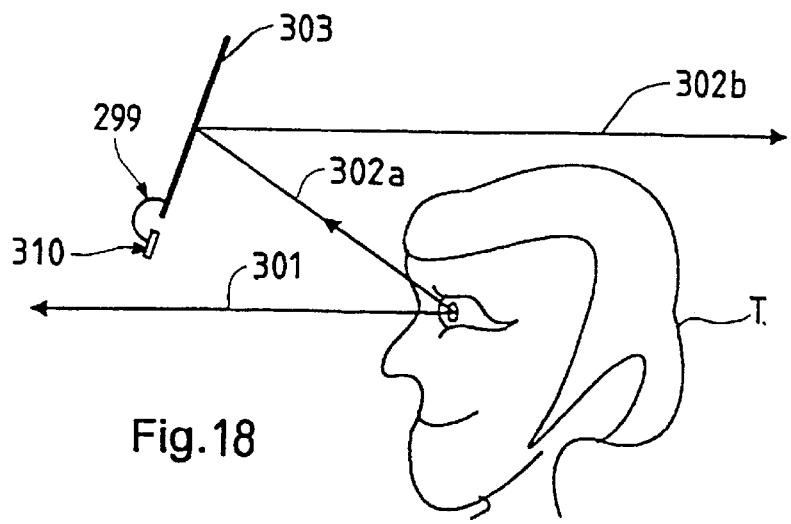
FIG. 18 is a side view illustrating a rear view mirror in combination with the drowsiness detection system of the invention.
Figure 19:
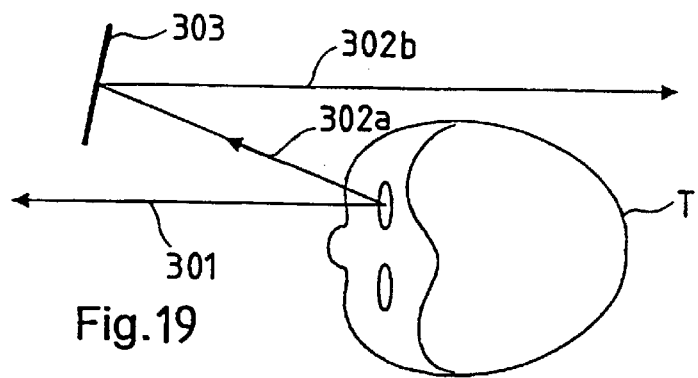
FIG. 19 is a top view illustrating operation of a rear view mirror.
Figure 20:
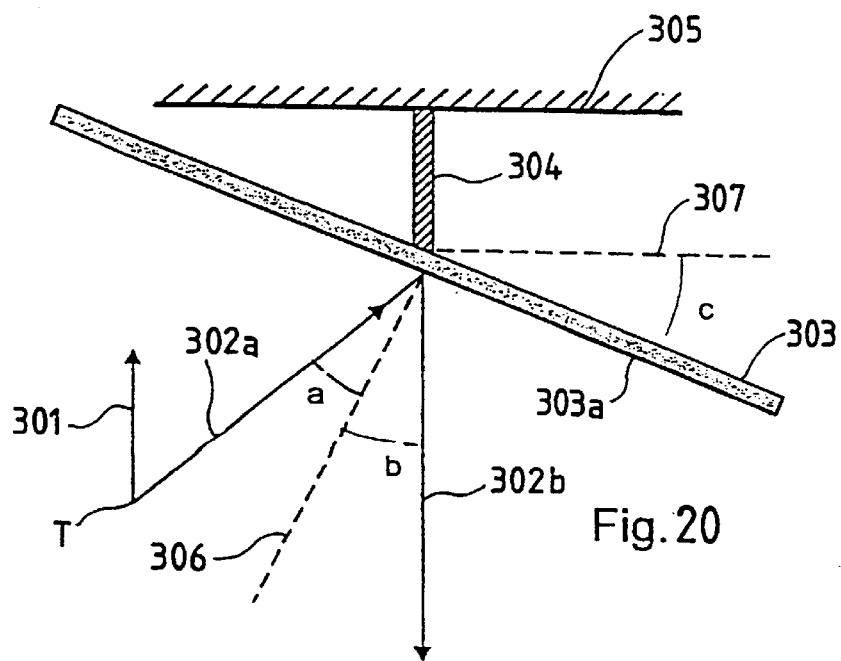
FIG. 20 is a schematic illustrating operation of a rear view mirror.

FIGS. 18 and 19 show a conventional rear-view mirror arrangement in which a driver T can see ahead along direction 301 and rearward (via rays 302a and 302b) through a rear-view mirror 303. Referring to FIG. 20, mirror 303 is attached to the vehicle body 305 through a connecting arm 304 which enables adjustment of vision axes 302a and 302b. Axes 301 and 302b are generally parallel and are oriented in the direction of the vehicle. Optical axis 306, which is perpendicular to the face 303a of mirror 303, divides the angle formed by axes 302a and 302b into equal angles a and b. Axis 307, which is perpendicular to axis 302b and therefore generally parallel to the attachment portion of vehicle body 305, defines an angle c between axis 307 and mirror face 303a which is generally equal to angles a and b. A camera or sensor 310 is preferably mounted to the mirror by means of a bracket 299. The camera may be mounted in any desired position to enable the driver to have a clear view of the road while enabling sensor 310 to acquire images of the face of the driver. Bracket 299 may be an adjustable bracket, enabling the camera to be faced in a desired direction, i.e., toward the driver, or may be at a fixed orientation such that when the mirror is adjusted by drivers of different sizes, the camera continues to acquire the face of the driver. The signal from the camera is communicated to the image processing system, which operates as described below, by means of lead wires or the like (not shown in FIGS. 18–20).

Figure 21:
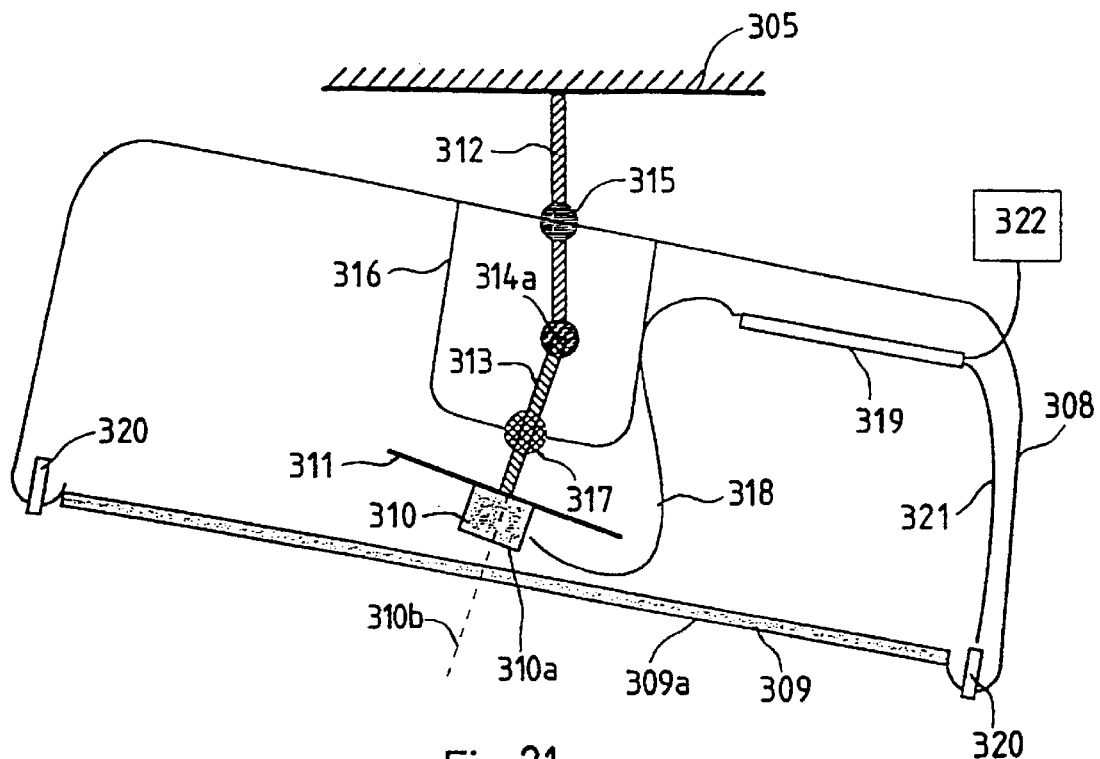
FIG. 21 is a cross-sectional top view illustrating a rear view mirror assembly incorporating the drowsiness detection system of the invention.
Figure 22:
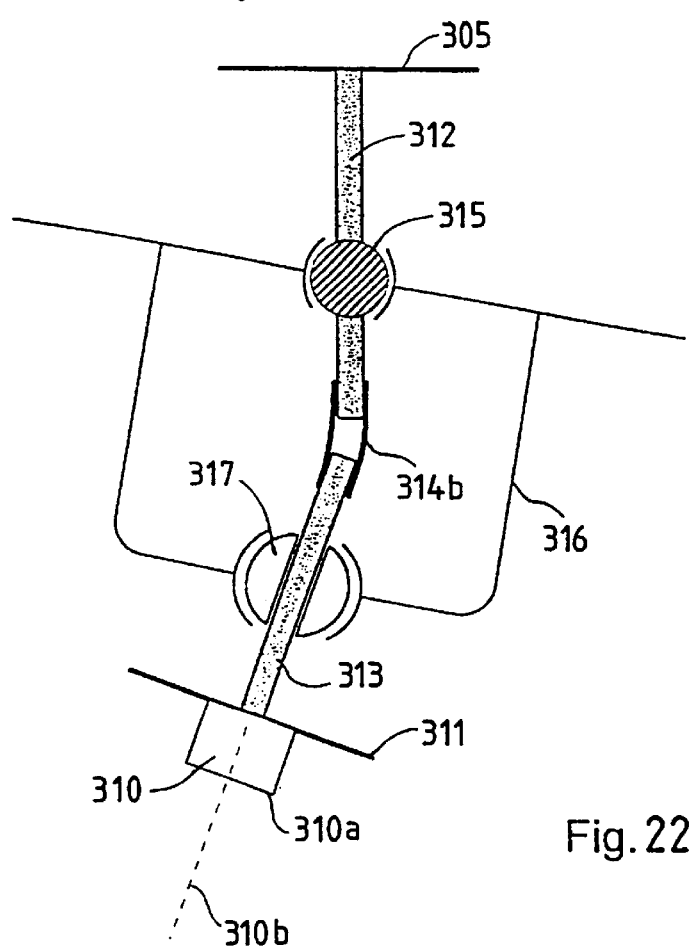
FIG. 22 is a partial cross-sectional top view illustrating a joint supporting the drowsiness detection system of the invention in the mirror assembly of FIG. 21.

FIGS. 21 and 22 show a rear-view mirror assembly 308 in which sensor 310 is mounted interior to the mirror assembly. Mirror assembly 308 is adapted so that as A assembly 308 is adjusted by a driver, sensor 310 remains directed toward the face of the driver. Rear-view mirror assembly 308 includes a two-way mirror 309 having a face 309a, movably oriented to provide a rear view to the driver. Sensor 310, which is preferably an electronic mini-camera or MOS sensor with a built-in lens, is axed to a bracket 311, is oriented facing the driver using a mechanical arrangement that enables sensor 310 to receive an image of the face of the driver when mirror 309 is adjusted so that the driver has a rear view of the vehicle. The mechanical arrangement consists of a Cardan type mechanical joint, which causes automatic adjustment of the bracket 311 when the driver adjusts the rear view mirror so that the receiving face 310a of sensor 310 receives the image of the face of the driver, i.e., optical axis 310b remains aligned toward the head of the driver.

Bracket 311 includes rods 312 and 313 that are movably coupled together by a pivot pin 314a (FIG. 21) or a sleeve 314b (FIG. 22). Rod 312 is attached at one end to a mounting portion of the vehicle 305. A pivot pin 315, which preferably consists of a ball and two substantially hemispherical caps, facilitates movement of mirror assembly 308. Rod 312 extends through pivot pin 315, and attaches to rod 313 via a sleeve 314b or another pivot pin 314a. At one end, rod 313 rigidly supports bracket 311 on which sensor 310 is mounted. Rod 313 extends through clamp 316 of mirror assembly 308 via a hollow pivot 317. Pivot 317 includes a ball having a channel therethrough in which rod 313 is engaged, and which rotates in substantially hemispherical caps supported by clamp 316. The joint constantly maintains a desired angle between mirror 309 and bracket 311, thereby permitting normal adjustment of rear-view mirror 309 while bracket 311 adjusts the direction of sensor 310 so that the face 310a of the sensor will receive an image of the face of the driver. If desired, it is foreseen that sensor 310 may be mounted interior to rear-view mirror assembly 308 at a fixed angle relative to the face 309a of the mirror assembly, provided that sensor 310 is able to receive an image of the face of the driver when the mirror is adjusted to drivers of different sizes. A wide angle lens may be mounted to sensor 310 to better enable the sensor to be used under different adjustment at circumstances.

Sensor 310 is connected by means of one or more lead wires 318 to image processor 319, which is preferably an image processing system of the type discussed above and is preferably in the form of an integrated circuit inside rear-view mirror assembly 308. In a preferred embodiment, image processing system 319 is integrally He constructed with sensor 310. Alternatively, image processing system 319 may be located exterior to mirror assembly 308 by means of conventional lead wires. While controller 319 is preferably a microprocessor, it is foreseen that controller 319 may be an ASIC or simple controller designed to perform the functions specified herein, particularly if the system is embedded, e.g. contained in a mirror assembly or integral with a vehicle.

Electroluminescent diodes 320 may be incorporated in mirror assembly 308 to illuminate the face of the driver with infrared radiation when ambient light is insufficient for image processing system 319 to determine the blinking characteristics of the driver. When such diodes are in use, sensor 310 must be of the type capable of receiving infrared radiation. Illumination of electroluminescent diodes 320 may be controlled by controller 42 (FIG. 12) of image processing system 319, if desired. For example, controller 42 may illuminate electroluminescent diodes 320 in the event that the histograms generated by image processing system 319 do not contain sufficient useful information to detect the features of the driver's face required, e.g., NBPTS is below a threshold. Electroluminescent diodes 320 may be illuminated gradually, if desired, and may operate in connection with one or more photocells (not shown) that generate a signal as to the ambient lighting near the driver, and which may be used to control electroluminescent diodes 320, either alone or in combination with controller 42 or another control circuit. If desired, an IR or other source of EMF radiation may be used to illuminate the face of the driver at all times, provided that sensor 310 is compatible with the illumination source. This eliminates many problems that may be associated with the use of ambient lighting to detect drowsiness.

An optional alarm 322, which may be for example a buzzer, bell or other notification means, may be activated by controller 42 upon detecting that the driver is falling asleep. All of the components contained in mirror assembly 308, and image processing system 319, are preferably powered by the electrical system of the vehicle.

Image processing system 319 monitors the alertness of the driver by detecting, in real time and on a continuous basis, the duration of the blinks of the driver's eyes and/or intervals between blinks, and by triggering alarm 322 to wake up the driver in the event the driver is detected falling asleep. Image processing system 319 receives an image of the face of the driver from sensor 310. The image may be of the complete face of the driver, or of a selected area of the driver's face that includes at least one eye of the driver. Image processing system 319 is capable of detecting numerous criteria that are associated with blinking eyes. These include any feature of the face that may be used to discern the closing of an eye, including detection of the pupil, retina, white, eyelids, skin adjacent to the eye, and others. The eye may also be detected by detecting either changes in the appearance of the eye when blinking or by detecting motion of the eyelid during blinking.

Figure 30:
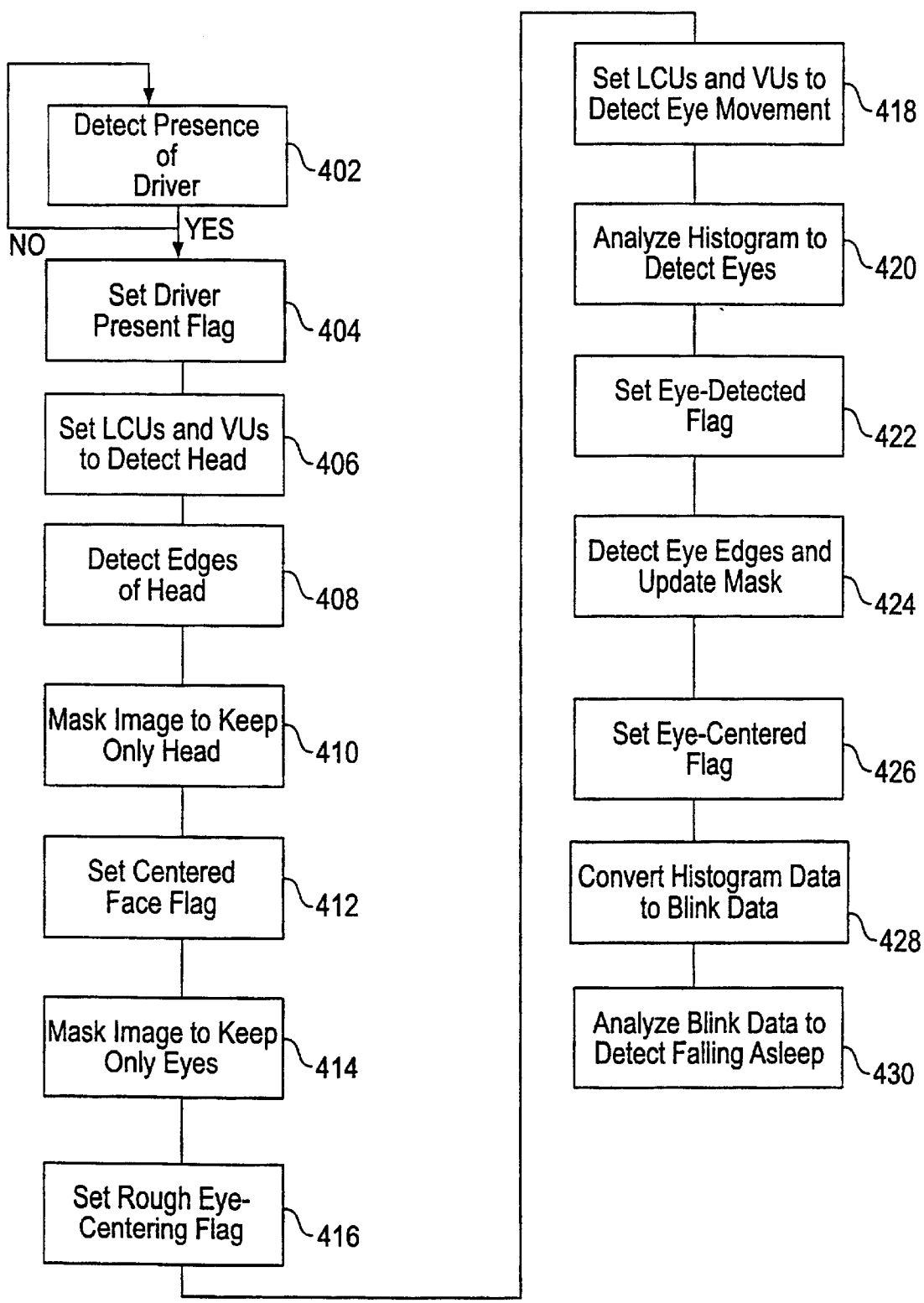
FIG. 30 is a flow diagram illustrating the use of the system of the invention to detect drowsiness.
Figure 31:
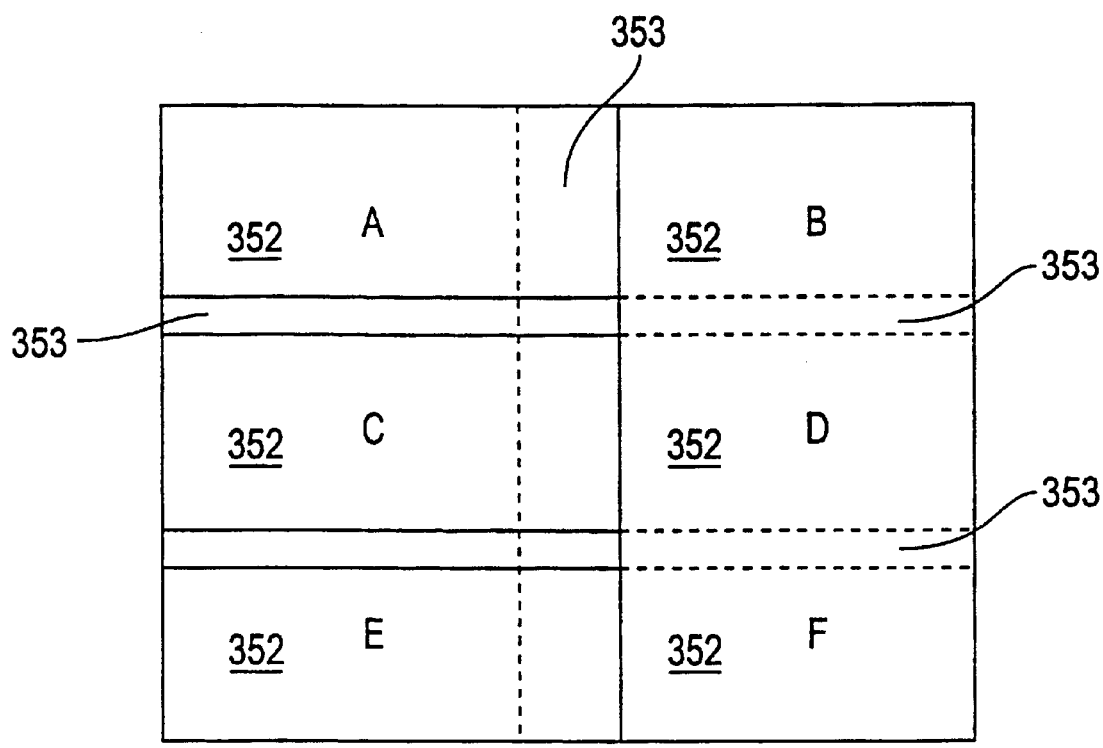
FIG. 31 illustrates the use of sub-images to search a complete image.

Referring to FIG. 30, as an initial step, the system of the invention preferably detects the presence of a driver in the driver's seat (402). This may be accomplished in any number of ways, such as by an electrical weight sensor switch in the driver's seat or by interfacing with a signal generated by the vehicle indicating that the vehicle is in use in motion, e.g., a speed sensor, a switch detecting that the vehicle is in gear, a switch detecting that closing of the seat belt, etc. Upon detection of such a signal, the system enters into a search mode for detecting the driver's face or driver's eye(s). Alternatively, since the system is powered by the electrical system of the vehicle, and more preferably by a circuit of the electrical system that is powered only when the vehicle is turned on, the system turns on only when the engine is turned on, and enters into a search mode in which it operates until the face or eye(s) of the driver are detected. Upon detection of a driver in the vehicle (404), a Driver Present flag is set to "1" so that controller 42 is aware of the presence of the driver.

As an alternative method of detecting the presence of the driver, if sensor is mounted in a manner that enables (or requires) that the sensor be adjusted toward the face of the driver prior to use, e.g., by adjustment of the rear-view mirror shown in FIG. 21, the system may activate an alarm until the sensor has acquired the face of the driver.

The driver may also be detected by using the image processing system to detect the driver entering the driver's seat. This assumes that the image processing system and sensor 310 are already powered when the driver enters the vehicle, such as by connecting the image processing system and sensor to a circuit of the vehicle electrical system that has constant power. Alternatively, the system may be powered upon detecting the vehicle door open, etc. When the driver enters the driver's seat, the image from sensor 310 will be characterized by many pixels of the image being in motion (DP=1), with CO having a relatively high value, moving in a lateral direction away from the driver's door. The pixels will also have hue characteristics of skin. In this embodiment, in a mode in which the system is trying to detect the presence of the driver, controller 42 sets the validation units to detect movement of the driver into the vehicle by setting the histogram formation units to detect movement characteristics of a driver entering the driver's seat. Most easily, controller 42 may set the validation units to detect DP=1, and analyze the histogram in the histogram formation unit for DP to detect movement indicative of a person entering the vehicle, e.g., NBPTS exceeding a threshold.

Figure 23:
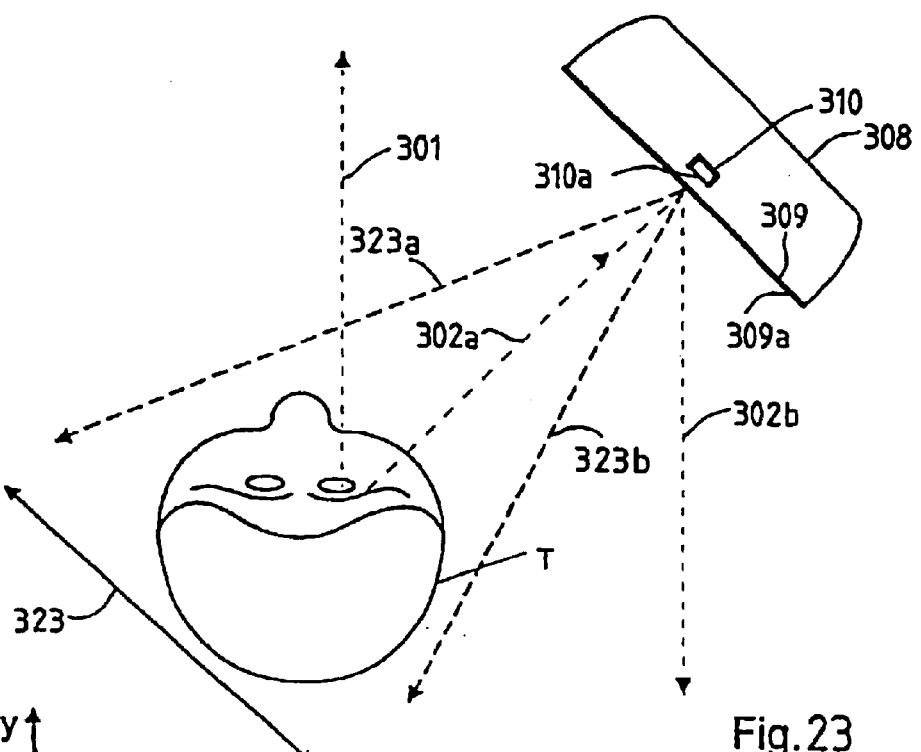
FIG. 23 is a top view illustrating the relationship between the rear view mirror assembly of FIG. 21 and a driver.

FIG. 23 shows the field of view 323 of sensor 310 between directions 323a and 323b where the head T of the driver is within, and is preferably centered in, conical field 323. Field 323 may be kept relatively narrow, given that the movements of the head T of the driver during driving are limited. Limitation of field 323 improves the sensitivity of the system since the driver's face will be represented in the images received from sensor 310 by a greater number of pixels, which improves the histogram formation process discussed below.

In general the number of pixels in motion will depend upon the field of view of the sensor. The ratio of the number of pixels characteristic of a driver moving into the vehicle to the total number of pixels in a frame is a function of the size of the field of vision of the sensor. For a narrow field of view (a smaller angle between 323a and 323b in FIG. 23), a greater number, and possibly more than 50% of the pixels will be "in movement" as the driver enters the vehicle, and the threshold will be greater. For a wide field of view (a greater angle between 323a and 323b in FIG. 23), a smaller number of pixels will be "in movement" as the driver enters the vehicle. The threshold is set corresponding to the particular location and type of sensor, and based upon other characteristics of the particular installation of the system. If NBPTS for the DP histogram exceeds the threshold, the controller has detected the presence of the driver.

As discussed above, other characteristics of the driver entering the vehicle may be detected by the system, including a high CO, hue, direction, etc., in any combinations, as appropriate, to make the system more robust. For example, controller 42 may set the linear combination units of the direction histogram formation unit to detect pixels moving into the vehicle, may set the linear combination unit for CO to detect high values, and/or may set the linear combination unit for hue to detect hues characteristic of human skin. Controller 42 may then set the validation units to detect DP, CO, hue, and/or direction, as appropriate. The resultant histogram may then be analyzed to determine whether NBPTS exceeds a threshold, which would indicate that the driver has moved into the driver's seat. It is foreseen that characteristics other than NBPTS of the resultant histogram may be used to detect the presence of the driver, e.g., RMAX exceeding a threshold.

When the driver has been detected, i.e., the Driver Present flag has been set to "1", the system detects the face of the driver in the video signal and eliminates from further processing those superfluous portions of the video signal above, below, and to the right and left of the head of the driver. In the image of the drivers head, the edges of the head are detected based upon movements of the head. The edges of the head will normally be characterized by DP=1 due to differences in the luminance of the skin and the background, even due to minimal movements of the head while the head is still. Movement of the head may be further characterized by vertical movement on the top and bottom edges of the head, and left and right movement on the vertical edges of the head. The pixels of the head in movement will also be characterized by a hue corresponding to human skin and relatively slow movement as compared to eyelid movement for example. Controller 42 preferably sets the linear combination unit of DP to detect DP=1 and sets the linear combination unit for direction to detect vertical and horizontal movement only (406). Optionally, the linear combination units for velocity and hue may be set to detect low velocities and human skin hues to make the system more robust. Also, the linear combination unit for CO may be set to eliminate the very fast movements characteristic of eye blinking in order to prevent the eyes from being considered at this stage of processing during which the head is being detected. Finally, controller 42 sets the validation units for DP, direction, and x and y position to be "on" (406). Optionally, the validation units for velocity, hue, and CO may be set "on" if these criteria are being detected.

Figure 24:
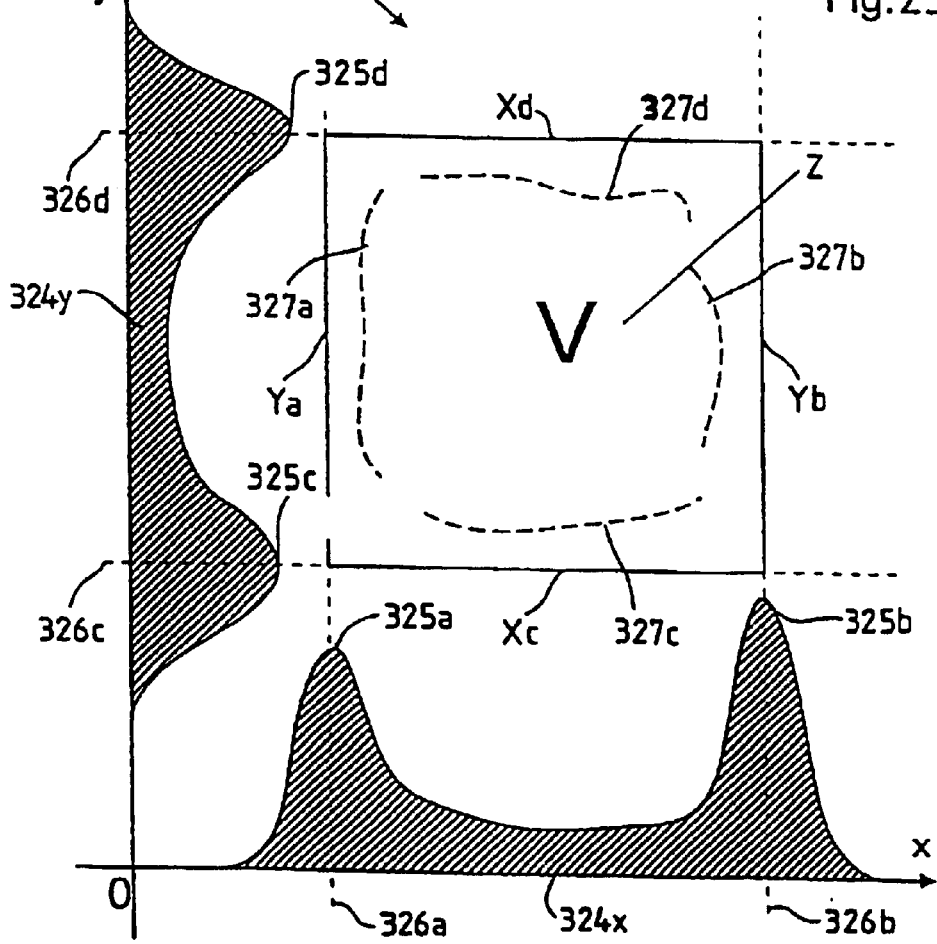
FIG. 24 illustrates detection of the edges of the head of a person using the system of the invention.

As illustrated in FIG. 24, the pixels having the selected characteristics are formed into histograms 324x and 324y along axes Ox and Oy, i.e., horizontal and vertical projections, respectively. Slight movements of the head of the driver having the characteristics selected are indicated as ripples 327a, 327b, 327c and 327d, which are shown in line form but which actually extend over a small area surrounding the periphery of the head. Peaks 325a and 325b of histogram 324x, and 325c and 325d of histogram 324y delimit, by their respective coordinates 326a, 326b, 326c and 326d, a frame bounded by straight lines Ya, Yb, Xc, Xd, which generally correspond to the area in which the face V of the driver is located. Controller 42 reads the histograms 324x and 324y from the histogram formation units, preferably during the blanking interval, and detects the locations of peaks 325a, 325b, 325c and 325d (408). In order to ensure that the head has been identified, the distance between peaks 325a and 325b and between peaks 325b and 325c are preferably tested to fall with a range corresponding to the normal ranges of human head sizes.

Figure 25:
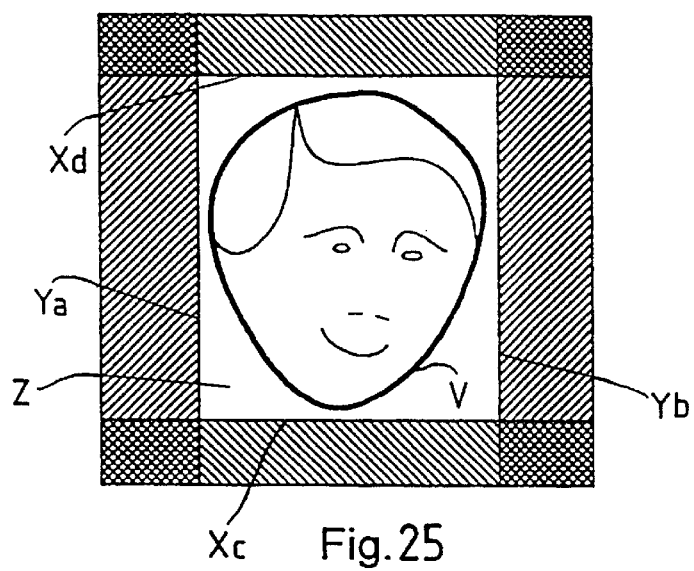
FIG. 25 illustrates masking outside of the edges of the head of a person.

Once the location of coordinates 326a, 326b, 326c and 326d has been established, the area surrounding the face of the driver is masked from further processing (410). Referring to FIG. 25, this is accomplished by having controller 42 set XMIN, XMAX, YMIN and YMAX to correspond to Xc, Xd, Ya, and Yb respectively. This masks the cross-hatched area surrounding face V from further consideration, which helps to eliminate background movement from affecting the ability of the system to detect the eye(s) of the driver. Thus, for subsequent analysis, only pixels in central area Z, framed by the lines Xc, Xd, Ya, Yb and containing face V are considered. As an alternative method of masking the area outside central area Z, controller 42 may set the semi-graphic memory 50 (FIG. 12) to mask off these areas. As indicated above, the semi-graphic memory may be used to mask off selected pixels of the image in individual or small rectangular groups. Since head V is not rectangular, use of the semi-graphic memory enables better masking around the rounded edges of the face to better eliminate background pixels from further consideration.

The process of detecting the head of the driver and masking background areas is repeated at regular intervals, and preferably once every ten frames or less. It is foreseen that this process may be repeated every frame, if desired, particularly if more than one set of histogram formation units is available for use. Controller 42 may also compute average values over time for coordinates 326a, 326b, 326c and 326d and use these values to set mask coordinates Xc, Xd, Ya, Yb, if desired. This will establish a nearly fixed position for the frame over time.

Figure 26:
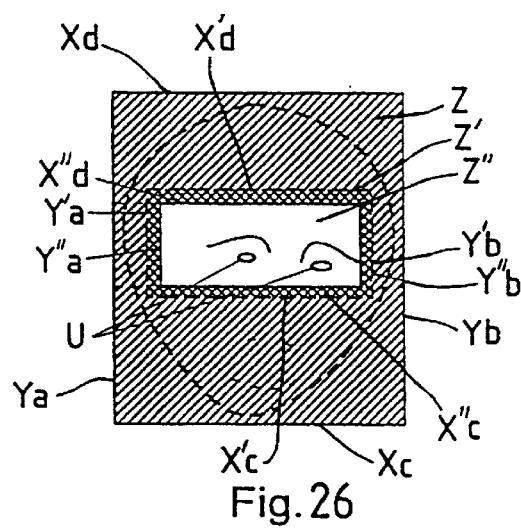
FIG. 26 illustrates masking outside of the eyes of a person.
Figure 27:
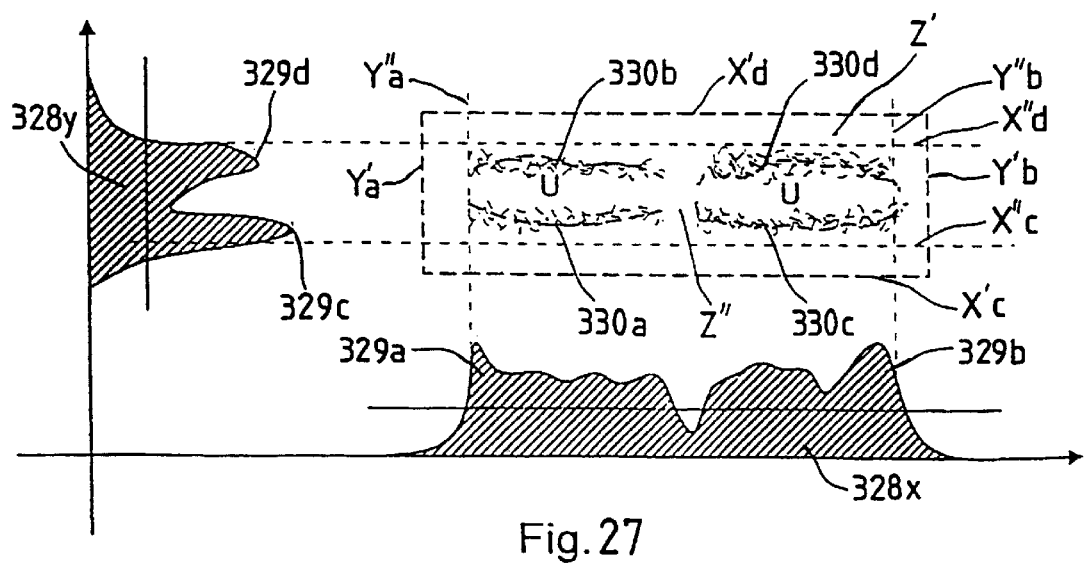
FIG. 27 illustrates detection of the eyes of a person using the system of the invention.

Once the frame has been established, a Centered-Face flag is set to "1" (412), and controller 42 initiates the process of reducing the frame size to more closely surround the eyes of the driver. Referring to FIG. 26, in which frame Z denotes the area bounded by Ya, Yb, Xc, Xd determined in the prior step, controller 42 initially uses the usual anthropomorphic ratio between the zone of the eyes and the entire face for a human being, especially in the vertical direction, to reduce the area under consideration to cover a smaller zone Z' bounded by lines Y'a, Y'b, X'c and X'd that includes the eyes U of the driver. Thus, the pixels in the outer cross-hatched area of FIG. 27 are eliminated from consideration and only the area within frame Z' is further considered. This is accomplished by having controller 42 set XMIN, XMAX, YMIN and YMAX to correspond to X'c, X'd, Y'a, and Y'b respectively (414). This masks the pixels in the area outside Z' from further consideration. Thus, for subsequent analysis, only pixels in area Z' containing eyes U are considered. As an alternative method of masking the area outside area Z', controller 42 may set the semi-graphic memory 50 to mask off these areas. It is foreseen that an anthropomorphic ratio may be used to set frame Z' around only a single eye, with detection of blinking being generally the same as described below, but for one eye only.

Once the area Z' is determined using the anthropomorphic ratio, a Rough Eye-Centering flag is set to "1" (416), and controller 42 performs the step of analyzing the pixels within the area Z' to identify movement of the eyelids. Movement of eyelids is characterized by criteria that include high speed vertical movement of pixels with the hue of skin. In general, within the area Z', formation of histograms for DP=1 may be sufficient to detect eyelid movement. This detection may be made more robust by detection of high values of CO, by detection of vertical movement, by detection of high velocity, and by detection of hue. As an alternative to detection of hue, movement of the pixels of the eye may be detected by detecting pixels with DP=1 that do not have the hue of skin. This will enable detection of changes in the number of pixels associated with the pupil, retina, iris, etc.

Controller 42 sets the linear combination unit for DP to detect DP=1 and sets the validation units for DP, and x and y position to be on (418). Optionally, the linear combination units and validation units may be set to detect other criteria associated with eye movement, such as CO, velocity, and hue. Initially, controller 42 also sets XMIN, XMAX, YMIN and YMAX to correspond to X'c, X'd, Y'a, and Y'b respectively. Referring to FIG. 27, a histogram is formed of the selected criteria, which is analyzed by controller 42 (420). If desired, a test is performed to ensure that the eyes have been detected. This test may, for example, consist of ensuring that NBTS in the histogram exceeds a threshold e.g., 20% of the total number of pixels in the frame Y'a, Y'b, X'c, X'd. Once the eyes have been detected an Eye-Detected flag is set to "1" (422).

FIG. 27 illustrates histogram 328x along axis Ox and histogram 328y along axis Oy of the pixels with the selected criteria corresponding to the driver's eyelids, preferably DP=1 with vertical movement. Controller 42 analyzes the histogram and determines peaks 329a, 329b, 329c and 329d of the histogram. These peaks are used to determine horizontal lines X"c and X"d and vertical lines Y"a and Y"b which define an area of movement of the eyelids Z", the movements of the edges of which are indicated at 330a and 330b for one eye and 330c and 330d for the other eye (424). The position of the frame bounded by Y"a, Y"b, X"c, X"d is preferably determined and updated by time-averaging the values of peaks 329a, 329b, 329c and 329d, preferably every ten frames or less. Once the eyes have been detected and frame Z" has been established an Eye Centered flag is set to "1" (426) and only pixels within frame Z" are thereafter processed.

Figure 28:
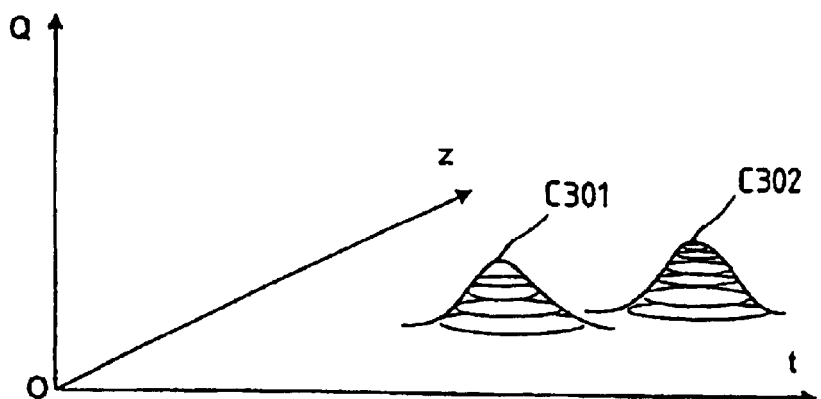
FIG. 28 illustrates successive blinks in a three-dimensional orthogonal coordinate system.

Controller 42 then determines the lengths of the eye blinks, and, if applicable, the time interval between successive blinks. FIG. 28 illustrates in a three-dimensional orthogonal coordinate system: OQ, which corresponds to the number of pixels in area Z" having the selected criteria; To, which corresponds to the time interval between successive blinks; and Oz which corresponds to the length of each blink. From this information, it is possible to determine when a driver is falling asleep. Two successive blinks C1 and C2 are shown on FIG. 28.

Figure 29:
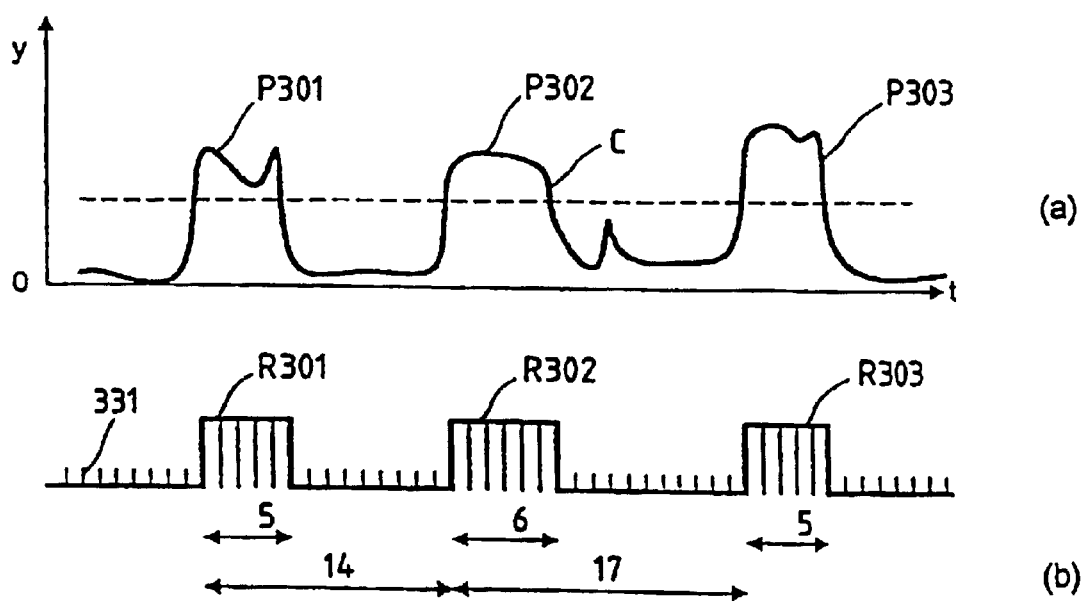
FIGS. 29A and 29B illustrate conversion of peaks and valleys of eye movement histograms to information indicative of blinking.

FIG. 29A illustrates on curve C the variation over time of the number of pixels in each frame having the selected criteria, e.g., DP=1, wherein successive peaks P1, P2, P3 correspond to successive blinks. This information is determined by controller 42 by reading NBPTS of the x and/or y histogram formation units. Alternatively, controller 42 may analyze the x and/or y histograms of the histogram formation units (FIG. 27) to detect peaks 329a and 329b and/or 329c and 329d, which over time will exhibit graph characteristics similar to those shown in FIG. 29A.

Controller 42 analyzes the data in FIG. 29A over time to determine the location and timing of peaks in the graph (428). This may be done, for example, as shown in FIG. 29B, by converting the graph shown in FIG. 29A into a binary data stream, in which all pixel counts over a threshold are set to "1", and all pixel counts below the threshold are set to "0" (vertical dashes 331), in order to convert peaks P1, P2, P3 to framed rectangles R1, R2 R3, respectively. Finally, FIG. 29B shows the lengths of each blink (5, 6, and 5 frames respectively for blinks P1, P2 and P3) and the time intervals (14 and 17 frames for the intervals between blinks P1 and P2, and P2 and P3 respectively). This information is determined by controller 42 through an analysis of the peak data over time.

Finally, controller 42 calculates the lengths of successive eye blinks and the interval between successive blinks (430).

If the length of the blinks exceeds a threshold, e.g., 350 ms, a flag is set to "1" indicating that the blink threshold has been exceeded. If the time interval between successive blinks is found to vary significantly over time, a flag is set to "1" indicting a variable intervals between blinks. Upon setting the first flag, which indicates that the driver is blinking at a rate indicative of falling asleep, controller 42 triggers alarm 322 for waking up the driver. The second flag may be used either to generate an alarm in the same manner as with the first flag, or to reinforce the first flag to, for example, increase the alarm sound level.

FIGS. 31–36 show an alternative method by which the generic image processing system may be used to detect a driver falling asleep. Initially, controller 42 is placed in a search mode (350) (FIG. 35), in which controller 42 scans the image to detect one or more image. It is also foreseen that the entire image may be searched at once for the nostrils, if desired.

Controller 42 sets XMIN, XMAX, YMRN, and YMAX to correspond to the first sub-image A (354). Controller 42 then sets the registers 106 in the luminance linear combination unit to detect low luminance levels (356). The actual luminance level selected will vary depending upon various factors, such as ambient lighting, time of day, weather conditions, etc. Keeping in mind that controller 42 is able to access the histogram calculated for luminance from histogram formation unit 24, controller 42 may use a threshold or other desired technique to select the desired luminances to search for the nostrils, e.g., selecting the lowest 15% of luminance values for consideration, and all may adapt the threshold as desired. Controller 42 also sets the validation units for luminance and x and y histogram on (358), thereby causing x and y histograms to be formed of the selected low luminance levels. Controller 42 then analyzes the x and y direction histograms to identify characteristics indicative of the nostrils, as discussed below (360). If nostrils are not identified (362), controller 42 repeats this process on the next sub-image, i.e., sub-image B, and each subsequent sub-image, until nostrils are identified, repeating the process starting with sub-image A if required. Each sub-image is analyzed by controller 42 in a single frame. Accordingly, the nostrils may generally be acquired by the system in less than six frames. It is foreseen that additional sub-images may be used, if desired. It is also foreseen that the area in which the sub-images are searched may restricted to an area in which the nostrils are most likely to be present, either as determined from past operation of the system, or by use of an anthropomorphic model. For example, the outline of the head of the driver may be determined as described above, and the nostril search may then be restricted to a small sub-area of the image. It is also foreseen that the entire image may be search at once for the nostrils, if desired.

While the invention is being described with respect to identification of the nostrils as a starting point to locating the eyes, it is foreseen that any other facial characteristic, e.g., the nose, ears, eyebrows, mouth, etc., and combinations thereof, may be detected as a starting point for locating the eyes. These characteristics may be discerned from any characteristics capable of being searched by the system, including CO, DP, velocity, direction, luminance, hue and saturation. It is also foreseen that the system may locate the eyes directly, e.g., by simply searching the entire image for DP=1 with vertical movement (or any other searchable characteristics of the eye), without the need for using another facial criteria as a starting point. In order to provide a detailed view of the eye while enabling detection of the head or other facial characteristic of the driver, it is foreseen that separate sensors may be used for each purpose.

Figure 32:
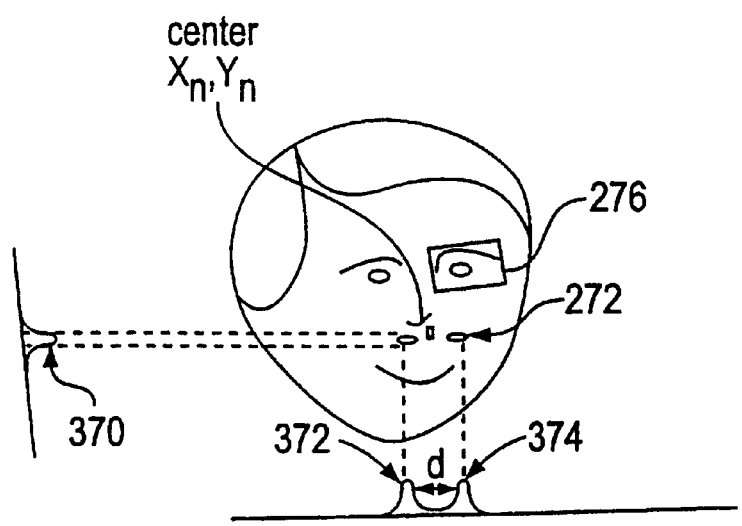
FIG. 32 illustrates the use of the system of the invention to detect nostrils and to track eye movement.

FIG. 32 shows sample x and y histograms of a sub-image in which the nostrils are located. Nostrils are characterized by a peak 370 in the y-direction histogram, and two peaks 372 and 374 in the x-direction histogram. Confirmation that the nostrils have been identified may be accomplished in several ways. First, the histograms are analyzed to ensure that the characteristics of each histogram meets certain conditions. For example, NBPTS in each histogram should exceed a threshold associated with the normal number of pixels detectable for nostrils. Also, RMAX in the y histogram, and each peak of the x histogram should exceed a similar threshold. Second, the distance between nostrils d is fairly constant. The x histogram is analyzed by controller 42 and d is measured to ensure that it falls within a desired range. Finally, the width of a nostril is also fairly constant, although subject to variation due to shadowing effects. Each of the x and y histograms is analyzed by controller 42 to ensure that the dimensions of each nostril fall within a desired range. If the nostrils are found by controller 42 to meet these criteria, the nostrils have been acquired and the search mode is ended. If the nostrils have not been acquired, the search mode is continued. Once the nostrils are acquired, the x position of the center of the face (position d/2 within the sub-image under consideration) is determined, as is the y location of the nostrils in the image (POSRMAX of the y histogram) (364).

In the present example, only a single eye is analyzed to determine when the driver is falling asleep. In this case the shadow of the eye in the open and closed positions is used to determine from the shape of the shadow whether the eye is open or closed. As discussed above, for night-time applications, the invention is preferably used in combination with a short-wave IR light source. For the presently described example, the IR light source is preferably positioned above the driver at a position to cast a shadow having a shape capable of detection by the system. The anthropomorphic model is preferably adaptive to motion; to features of the driver, and to angular changes of the driver relative to the sensor.

Figure 36:
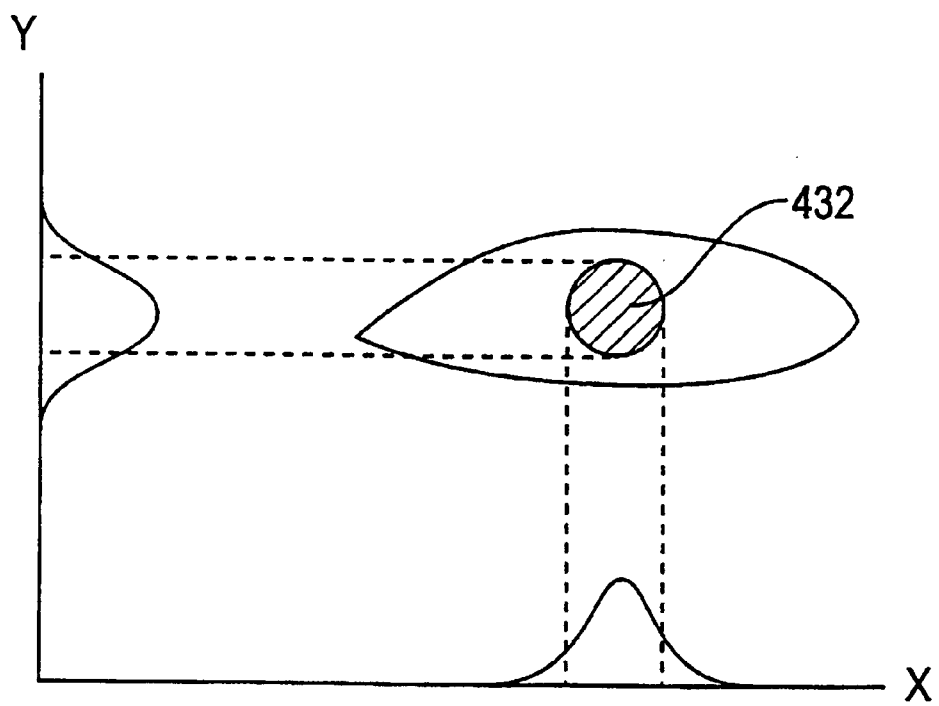
FIG. 36 illustrates use of the system to detect a pupil.

Referring to FIG. 32, having determined the location of the nostrils 272 of the driver having a center position $X_N$, $Y_N$, a search box 276 is established around an eye 274 of the driver (366). The location of search box 276 is set using an anthropomorphic model, wherein the spatial relationship between the eyes and nose of humans is known. Controller 42 sets XMIN, XMAX, YMIN, and YMAX to search within the area defined by search box 276. Controller 42 further sets the luminance and x and y direction histograms to be on, with the linear combination unit for luminance set to detect low histogram levels relative to the rest of the image, e.g., the lowest 15% of the luminance levels (368). As a confirmation of the detection of the nostrils or other facial feature being detected, search box 276, which is established around an eye of the driver using an anthropomorphic model, may be analyzed for characteristics indicative of an eye present in the search box. These characteristics may include, for example, a moving eyelid, a pupil, iris or cornea, a shape corresponding to an eye, a shadow corresponding to an eye, or any other indica indicative of an eye. Controller 42 sets the histogram formation units to detect the desired criteria. For example, FIG. 36 shows a sample histogram of a pupil 432, in which the linear combination units and validation units are set to detect pixels with very low luminance levels and high gloss that are characteristic of a pupil. The pupil may be verified by comparing the shapes of the x and y histograms to known characteristics of the pupil, which are generally symmetrical, keeping in mind that the symmetry may be affected by the angular relationship between the sensor and the head of the driver.

Upon detection of the desired secondary facial criteria, identification of the nostrils is confirmed and detection of eye openings and closings is initiated. Alternatively, the criteria being detected to confirm identification of the nostrils may be eye blinking using the technique described below. If no blinking is detected in the search box, the search mode is reinitiated.

Blinking of the eye is detected during a tracking mode 400. In the tracking mode controller 42 sets XMIN, XMAX, YMIN, and YMAX to search within the area defined by search box 276. Controller 42 further sets the luminance and x and y direction histograms to be on, with the linear combination unit for luminance set to detect low histogram levels relative to the rest of the image, e.g., the lowest 15% of the luminance levels (368), in order to detect shadowing of the eye. During the tracking mode, the system monitors the location of nostrils 272 to detect movement of the head. Upon detected movement of the head, and a resultant shift in the position of $X_N$, $Y_N$, search box 276 is shifted according to the anthropomorphic model to retain the search box over the eye of the driver.

Figure 33:
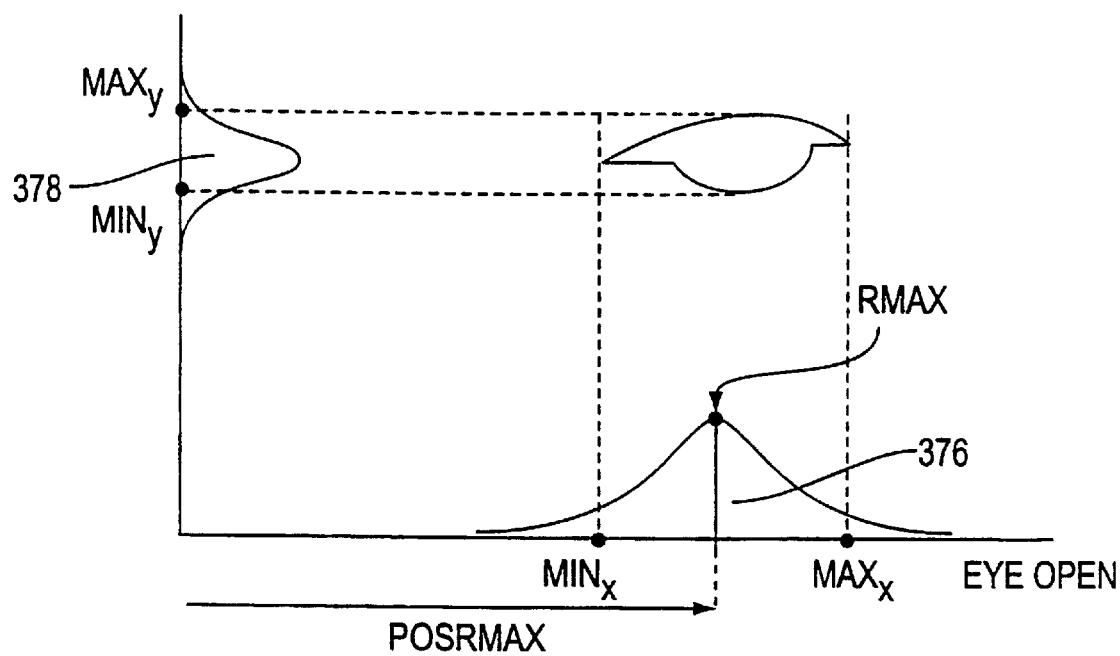
FIG. 33 illustrates the use of the system of the invention to detect an open eye.
Figure 34:
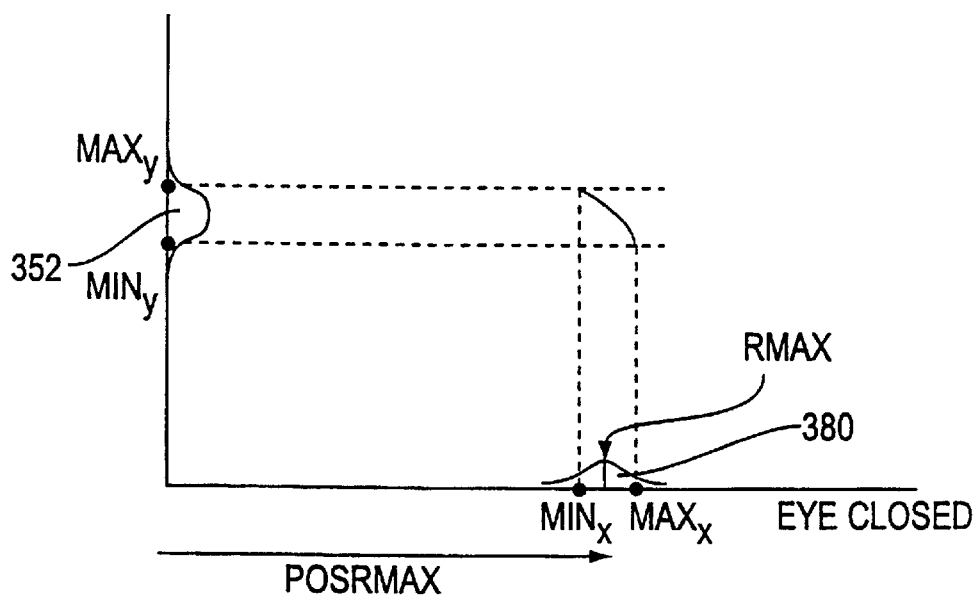
FIG. 34 illustrates the use of the system of the invention to detect a closed eye.
Figure 35:
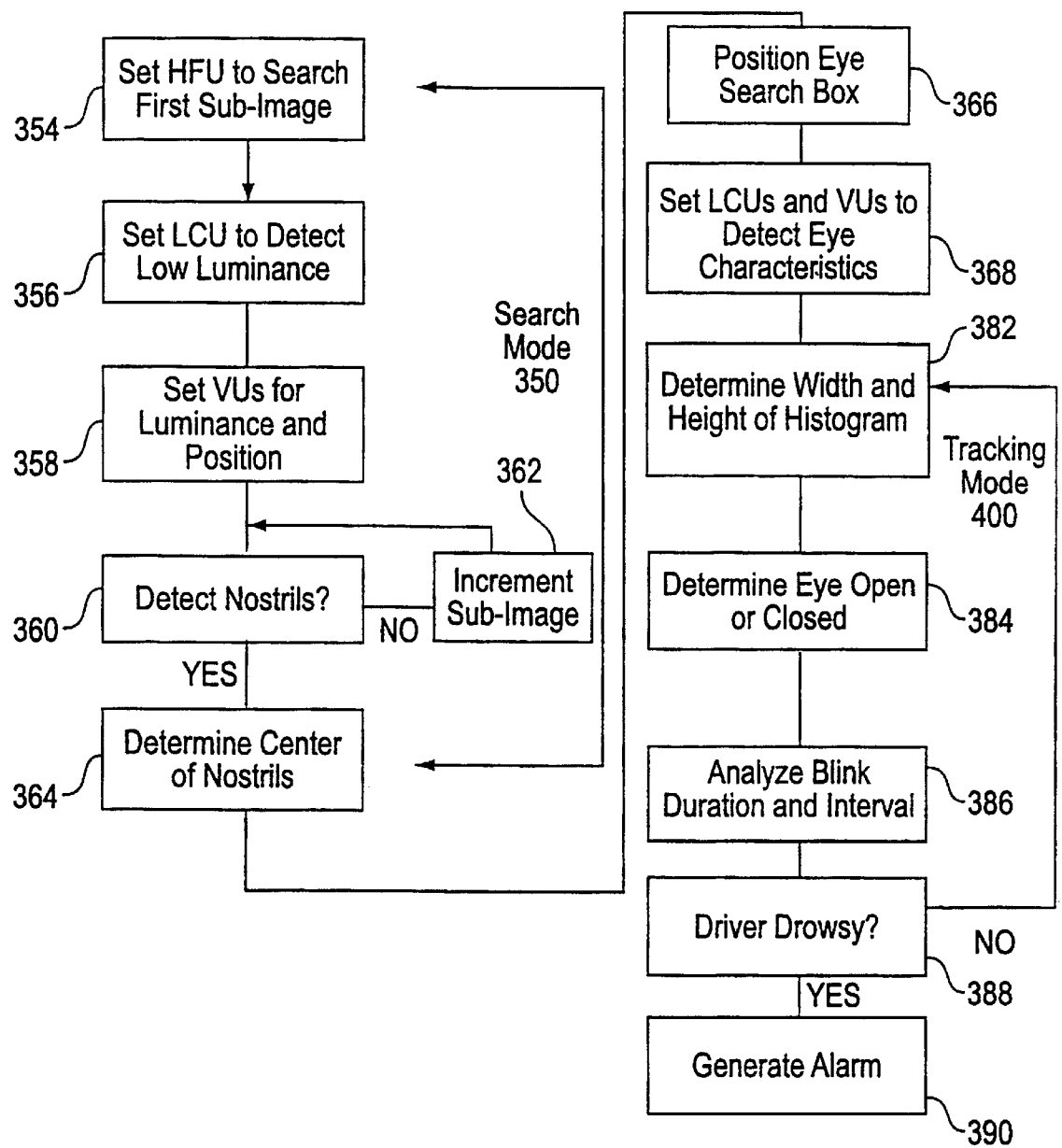
FIG. 35 is a flow diagram of an alternative method of detecting drowsiness.

FIG. 33 shows the shapes of the x and y histograms 376, 378 with the eye open, and FIG. 34 shows the shapes of the x and y histograms 380, 382 with the eye closed. The shapes of the shadows, and especially the shape of the shadow with the eye closed will vary depending upon the location of the camera and the location of the light source creating the shadow, e.g., the sun or the IR light source. In any case, the width $MAX_x-MIN_x$ and the height $MAX_y-MIN_y$ of each histogram will generally be significantly greater for an open eye than for a closed eye. Controller 42 analyzes the width and height of each histogram to determine when the eye is open and when it is closed (382). An open eye may be determined by any number of characteristics of the x and y histograms, including width $MA_x-MIN_x$ and height $MAX_y-MIN_y$ exceeding thresholds, NBPTS of each histogram exceeding a threshold, RMAX of each histogram exceeding a threshold, change in position of POSRMAX as compared to a closed eye, etc. Similarly, a closed eye may be determined by any number of characteristics of the x and y histograms, including width $MAX_x-MIN_x$ and height $MAX_y-MIN_y$ being below thresholds, NBPTS of each histogram being below a threshold, RMAX of each histogram being below a threshold, change in position of POSRMAX as compared to an open eye, etc., In a preferred embodiment, controller 42 calculates the width $MAX_x-MIN_x$ and height $MAX_y-MIN_y$ of each histogram and utilizes thresholds to determine whether the eye is open or closed. If each width $MAX_x-MIN_x$ and height $MAX_y-MIN_y$ exceed thresholds, the eye is determined to be open. If each of width $MAX_x-MIN_x$ and height $MAX_y-MIN_y$ fall below thresholds (which may be different from the thresholds used to determine an open eye), the eye is determined to be closed (384). MAX and MIN are preferably the MAX and MIN calculated in the histogram formation units. On the other hand, MAX and MIN may be other thresholds, e.g., the points on the histograms corresponding to RMAX/2 or some other threshold relative to RMAX.

Controller 42 analyzes the number of frames the eye is open and closed over time to determine the duration of each blink and/or the interval between blinks (386). Using this information, controller 42 determines whether the driver is drowsy (388). Upon determining that the driver is drowsy, controller 42 generates an alarm to awaken the driver (390) or another signal indicative that the driver is sleeping.

Controller 42 constantly adapts operation of the system, especially in varying lighting levels. Controller 42 may detect varying lighting conditions by periodically monitoring the luminance histogram and adapting the gain bias of the sensor to maintain as broad a luminance spectrum as possible. Controller 42 may also adjust the thresholds that are used to determine shadowing, etc. to better distinguish eye and nostril shadowing from noise, e.b.v.c.x.g. shadowing on the side of the nose, and may also adjust the sensor gain to minimize this effect. If desired controller 42 may cause the histogram formation units to form a histogram of the iris. This histogram may also be monitored for consistency, and the various thresholds used in the system adjusted as necessary.

It will be appreciated that while the invention has been described with respect to detection of the eyes of a driver using certain criteria, the invention is capable of detecting any criteria of the eyes using any possible measurable characteristics of the pixels, and that the characteristics of a driver falling asleep may be discerned from any other information in the histograms formed by the invention. Also, while the invention has been described with respect to detecting driver drowsiness, it is applicable to any application in which drowsiness is to be detected. More generally, although the present invention has been described with respect to certain embodiments and examples, variations exist that are within the scope of the invention as described in the following claims.

What is claimed is:

1. A process of detecting a person falling asleep, the process comprising:
   acquiring an image of the face of the person;
   identifying a sub-area of the image comprising at least one eye of the person, including:
      identifying the head of the person in the image; and
      identifying the sub-area of the image using an anthropomorphic model;
      selecting pixels within the sub-area of the image having characteristics corresponding to characteristics of the at least one eye of the person;
      forming at least one histogram of the selected pixels;
      analyzing the at least one histogram over time to identify each opening and closing of the eye; and
      determining from the opening and closing information of the eye, characteristics indicative of a person falling asleep.

2. The process according to claim 1 wherein identifying the head of the person in the image comprises:
   selecting pixels of the image having characteristics corresponding to edges of the head of the person;
   forming histograms of the selected pixels projected onto forthogonal axes; and
   analyzing the histograms of the selected pixels to identify the edges of the head of the person.

3. A process of detecting a person falling asleep, the process comprising:
   acquiring an image of the face of the person;
   identifying a sub-area of the image comprising at least one eye of the person, including:
      identifying the location of a facial characteristic of the person in the image; and
      identifying the sub-area of the image using an anthropomorphic model and the location of the facial characteristic;
      selecting pixels within the sub-area of the image having characteristics corresponding to characteristics of the at least one eye of the person;

forming at least one histogram of the selected pixels;
analyzing the at least one histogram over time to identify each opening and closing of the eye; and
determining from the opening and closing information of the eye, characteristics indicative of a person falling asleep.

4. The process according to claim 3 wherein the step of identify the location of a facial characteristic of the person in the image comprises the steps of:
selecting pixels of the image having characteristics corresponding to the facial characteristic;
forming histograms of the selected pixels projected onto orthogonal axes; and
analyzing the histograms of the selected pixels to identify the position of the facial characteristic in the image.

5. The process according to claim 4 wherein the facial characteristic is the nostrils of the person, and wherein the step of selecting pixels of the image having characteristics corresponding to the facial characteristic comprises selecting pixels having low luminance levels.

6. The process according to claim 5 further comprising the step of analyzing the histograms of the nostril pixels to determine whether the spacing between the nostrils is within a desired range and whether the dimensions of the nostrils fall within a desired range.

7. The process according to claim 5 wherein the step of identifying the location of a facial characteristic of the person in the image comprises the step of searching sub-images of the image to identify the nostrils.

8. The process according to claim 3 wherein the step of identifying the location of a facial characteristic of the person in the image comprises the step of searching sub-images of the image to identify the facial characteristic.

9. The process according to claim 8 wherein the facial characteristic is a first facial characteristic and further comprising the steps of:
using an anthropomorphic model and the location of the first facial characteristic to select a sub-area of the image containing a second facial characteristic;
selecting pixels of the image having characteristics corresponding to the second facial characteristic; and
analyzing the histograms of the selected pixels of the second facial characteristic to confirm the identification of the first facial characteristic.

10. A process of detecting a person falling asleep, the process comprising the steps of
acquiring an image of the face of the person;
selecting pixels of the image having characteristics corresponding to characteristics of at least one eye of the person;
forming at least one histogram of the selected pixels;
analyzing the at least one histogram over time to identify each opening and closing of the eye; and
determining from the opening and closing information of the eye, characteristics indicative of a person falling asleep;
wherein the step of selecting pixels of the image comprises selecting pixels having low luminance levels corresponding to shadowing of the eye; and
wherein the step of analyzing the at least one histogram comprises analyzing the shape of the eye shadowing to determine openings and closings of the eye.

11. The process according to claim 10 wherein the step of forming at least one histogram of the selected pixels comprises forming histograms of shadowed pixels of the eye projected onto orthogonal axes, and wherein the step of analyzing the shape of the eye shadowing comprises analyzing the width and height of the shadowing.

12. A process of detecting a person falling asleep, the process comprising the steps of:
acquiring an image of the face of the person;
selecting pixels of the image having characteristics corresponding to characteristics of at least one eye of the person;
forming at least one histogram of the selected pixels;
analyzing the at least one histogram over time to identify each opening and closing of the eye; and
determining from the opening and closing information of the eye, characteristics indicative of a person falling asleep;
wherein the step of selecting pixels of the image comprises selecting pixels in movement corresponding to blinking; and
wherein the step of analyzing the at least one histogram comprises analyzing the number of pixels in movement over time to determine openings and closings of the eye.

13. The process according to claim 12 wherein the step of selecting pixels of the image having characteristics corresponding to characteristics of at least one eye of the person comprises selecting pixels having one or more characteristics selected from the group consisting of i) parameter DP=1 indicative of significant variation, ii) time constant CO indicative of a blinking eyelid, iii) velocity indicative of a blinking eyelid, and iv) up and down movement indicative of a blinking eyelid.

14. An apparatus for detecting a person falling asleep, the apparatus comprising:
a sensor for acquiring an image of the face of the person, the image comprising pixels corresponding to the eye of the person;
a controller; and
a histogram formation unit for forming a histogram on pixels having selected characteristics,
the controller controlling the histogram formation unit to select pixels of the image having characteristics corresponding to characteristics of at least one eye of the person and to for a histogram of the selected pixels, the controller analyzing the histogram over time to identify each opening and closing of the eye, and determining from the opening and closing information on the eye, characteristics indicative of a person falling asleep;
the controller interacting with the histogram formation unit to identify a sub-area of the image comprising the at least one eye, and the controller controls the histogram formation unit to select pixels of the image having characteristics corresponding to characteristics of at least one eye only within the sub-area of the image;
the controller interacting with the histogram formation unit to identify the head of the person in the image; and
the controller identifies the sub-area of the image using an anthropomorphic model.

15. The apparatus according to claim 14 wherein:
the histogram formation unit selects pixels of the image having characteristics corresponding to edges of the head of the person and forms histograms of the selected pixels projected onto orthogonal axes; and
the controller analyzes the histograms of the selected pixels to identify the edges of the head of the person.

16. The apparatus according to claim 14 wherein:

the controller interacts with the histogram formation unit to identify the location of a facial characteristic of the person in the image; and the controller identifies the sub-area of the image using an anthropomorphic model and the location of the facial characteristic.

17. The apparatus according to claim 16 wherein:

the histogram formation unit selects pixels of the image having characteristics corresponding to the facial characteristic and forms histograms of the selected pixels projected onto orthogonal axes;

the controller analyzes the histograms of the selected pixels to identify the position of the facial characteristic in the image.

18. The apparatus according to claim 17 wherein the facial characteristic is the nostrils of the person, and wherein the histogram formation unit selects pixels of the image having low luminance levels corresponding to the luminance level of the nostrils.

19. The apparatus according to claim 18 wherein the controller analyzes the histograms of the nostril pixels to determine whether the spacing between the nostrils is within a desired range and whether the dimensions of the nostrils fall within a desired range.

20. The apparatus according to claim 18 wherein the controller interacts with the histogram formation unit to search sub-images of the image to identify the nostrils.

21. The apparatus according to claim 16 wherein the controller interacts with the histogram formation unit to search sub-images of the image to identify the facial characteristic.

22. The apparatus according to claim 21 wherein the facial characteristic is a first facial characteristic and further comprising:

the controller using an anthropomorphic model and the location of the first facial characteristic to cause the histogram formation unit to select a sub-area of the image containing a second facial characteristic, the histogram formation unit selecting pixels of the image in the sub-area having characteristics corresponding to the second facial characteristic and forming a histogram of such pixels; and the controller analyzing the histogram of the selected pixels corresponding to the second facial characteristic to confirm the identification of the first facial characteristic.

23. The apparatus according to claim 14 wherein:

the histogram formation unit selects pixels of the image having low luminance levels corresponding to shadowing of the eye; and wherein the controller analyzes the shape of the eye shadowing to determine openings and closings of the eye.

24. The apparatus according to claim 23 wherein histogram formation unit forms histograms of shadowed pixels of the eye projected onto orthogonal axes, and wherein the controller analyzes the width and height of the shadowing to determine openings and closings of the eye.

25. The apparatus according to claim 14 wherein:

the histogram formation unit selects pixels of the image in movement corresponding to blinking; and the controller analyzes the number of pixels in movement over time to determine openings and closings of the eye.

26. The apparatus according to claim 25 wherein the histogram formation units selects pixels of the image having characteristics of movement corresponding to blinking, such characteristics being selected from the group consisting of i) parameter DP=1 indicative of significant variation, ii) time constant CO indicative of a blinking eyelid, iii) velocity indicative of a blinking eyelid, and iv) up and down movement indicative of a blinking eyelid.

27. The apparatus according to claim 14 wherein the sensor is integrally constructed with the controller and the histogram formation unit.

28. The apparatus according to claim 14 further comprising an alarm, the controller operating the alarm upon detection of the person falling asleep.

29. The apparatus according to claim 14 further comprising an illumination source, the sensor being adapted to view the person when illuminated by the illumination source.

30. The apparatus according to claim 29 wherein the illumination source is a source of IR radiation.

31. A rear-view mirror assembly for a vehicle which comprises:

a rear-view mirror; and the apparatus according to claim 14 mounted to the rear-view mirror.

32. The rear-view mirror assembly according to claim 31 further comprising a bracket attaching the apparatus to the rear-view mirror.

33. The rear-view mirror assembly according to claim 31 further comprising a housing having an open side and an interior, the rear-view mirror being mounted to the open side of the housing, the rear view mirror being see-through from the interior of the housing to an exterior of the housing, the apparatus being mounted interior to the housing with the sensor directed toward the rear-view mirror.

34. The rear-view mirror assembly according to claim 33 further comprising a joint attaching the apparatus to the rear-view mirror assembly, the joint adapted to maintain the apparatus in a position facing a driver of the vehicle during adjustment of the mirror assembly by the driver.

35. The rear-view mirror assembly according to claim 31 further comprising a source of illumination directed toward the person, the sensor being adapted to view the person when illuminated by the source of illumination.

36. The rear-view mirror assembly according to claim 31 further comprising an alarm, the controller operating the alarm upon detection of the person falling asleep.

37. A rear-view mirror assembly which comprises:

a rear-view mirror; and the apparatus according to claim 14, the sensor being mounted to the rear-view mirror, the controller and the histogram formation unit being located remote from the sensor.

38. A vehicle comprising the apparatus according to claim 14.

39. A process of detecting a feature of an eye, the process comprising the steps of:

acquiring an image of the face of the person, the image comprising pixels corresponding to the feature to be detected;

identifying a characteristic of the face other than the feature to be detected;

identifying a portion of the image of the face comprising the feature to be detected using an anthropomorphic model based on the location of the identified facial characteristic;

selecting pixels of the portion of the image having characteristics corresponding to the feature to be detected;

forming at least one histogram of the selected pixels; and analyzing the at least one histogram over time to identify characteristics of the feature to be detected;

said feature being the iris, pupil or cornea.

* * * * *